(12) United States Patent
Conradson et al.

(10) Patent No.: US 10,914,735 B2
(45) Date of Patent: *Feb. 9, 2021

(54) PROTEIN DETECTION USING FET

(71) Applicant: LIFE TECHNOLOGIES CORPORATION, Carlsbad, CA (US)

(72) Inventors: Scott Conradson, Carlsbad, CA (US); David Dinauer, Fox Point, WI (US); Bin Zhao, Brown Deer, WI (US); Dmitriy Gremyachinskiy, San Francisco, CA (US); Jason Myers, Golden, CO (US); Jeffrey Rossio, Frederick, MD (US); Victoria Singer, Eugene, OR (US); Kristina Giorda, San Mateo, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/846,035

(22) Filed: Dec. 18, 2017

(65) Prior Publication Data

US 2018/0100194 A1    Apr. 12, 2018

Related U.S. Application Data

(63) Continuation of application No. 14/410,886, filed as application No. PCT/US2013/047726 on Jun. 25, 2013, now Pat. No. 9,885,083.

(Continued)

(51) Int. Cl.
*G01N 33/543* (2006.01)
*G01N 33/569* (2006.01)
(Continued)

(52) U.S. Cl.
CPC ..... *G01N 33/54373* (2013.01); *C12Q 1/6876* (2013.01); *G01N 33/543* (2013.01);
(Continued)

(58) Field of Classification Search
None
See application file for complete search history.

(56) References Cited

U.S. PATENT DOCUMENTS 9,885,083 B2   2/2018   Conradson et al.
2003/0114354 A1   6/2003   Feder et al.
(Continued)

FOREIGN PATENT DOCUMENTS

EP   2864786   4/2015
GB   2461127   12/2009
(Continued)

OTHER PUBLICATIONS

Brenner, S. et al. "Encoded Combinatorial Chemistry". Proc. Natl. Acad. Sci. USA 89, 5381-5383 (1992).
(Continued)

*Primary Examiner* — Melanie Brown

(57) ABSTRACT

Accordingly, in some embodiments methods for detecting an analyte or analytes in one or more sample(s) are provided. The methods encompass providing a solid support with an addressable marker and an associated ligand, contacting the solid substrate to a sample, thereby forming a contacted solid support, associating the contacted solid support with a FET array and detecting the electrical properties of the FET array and thereby detecting an analyte or analytes in one or more samples. In other embodiments, the sample encompasses a second addressable marker.

11 Claims, 9 Drawing Sheets

Specification includes a Sequence Listing.

Related U.S. Application Data

(60) Provisional application No. 61/664,090, filed on Jun. 25, 2012.

(51) Int. Cl.
  *G01N 35/00* (2006.01)
  *C12Q 1/6876* (2018.01)
  *G01N 33/68* (2006.01)

(52) U.S. Cl.
  CPC . *G01N 33/54326* (2013.01); *G01N 33/56977* (2013.01); *G01N 33/6854* (2013.01); *G01N 35/0098* (2013.01); *G01N 2333/4703* (2013.01)

(56) References Cited

U.S. PATENT DOCUMENTS

| | | |
|---|---|---|
| 2006/0003339 A1 | 1/2006 | Fuernkranz et al. |
| 2007/0082346 A1 | 4/2007 | Schelp et al. |
| 2007/0231790 A1 | 10/2007 | Su |
| 2007/1023179 | 10/2007 | Su |
| 2008/0268450 A1 | 10/2008 | Nam et al. |
| 2010/0261203 A1 | 10/2010 | Cicciarelli et al. |
| 2010/1026120 | 10/2010 | Cicciarelli et al. |
| 2010/0300895 A1* | 12/2010 | Nobile ............. B01L 3/502761 205/775 |
| 2013/0130364 A1 | 5/2013 | Seo et al. |
| 2014/0371097 A1 | 12/2014 | Conti et al. |
| 2015/0005178 A1 | 1/2015 | Bonin et al. |

FOREIGN PATENT DOCUMENTS

| | | |
|---|---|---|
| WO | 2005/043160 A2 | 5/2005 |
| WO | 2011/030159 A1 | 3/2011 |
| WO | WO-2014004587 A2 | 1/2014 |

OTHER PUBLICATIONS

Needels, M., et al., "Generation and screening of an oligonucleotide-encoded synthetic peptide library", Proc. Natl, Acad. Sci. USA,90, 1993, 10700-10704.
PCT/US2013/047726, International Preliminary Report on Patentability dated Dec. 31, 2014, 7 Pages.

* cited by examiner

PROTEIN DETECTION USING FET

PRIORITY CLAIM

This application is a Continuation application of U.S. application Ser. No. 14/410,886, having a 35 U.S.C. § 371 filing date of Dec. 23, 2014, now issued U.S. Pat. No. 9,885,083, which is a U.S. National Application filed under 35 U.S.C. 371 of PCT/US2013/047726 filed Jun. 25, 2013, which claims benefit of priority to U.S. provisional Application 61/664,090 filed Jun. 25, 2012, the contents of which applications are incorporated by reference in their entireties.

BACKGROUND

In many disciplines, such as medical diagnostics, environmental monitoring and chemical analysis, it is desirable to detect the presence of a given analyte in a solution. For example, detecting biological analytes such as bacteria, antigens, antibodies, receptors, ligands and nucleic acids is pivotal to diagnostic test methods for a wide variety of diseases and conditions and is important to research, forensics and risk assessment applications.

Typical methods for detecting biological analytes rely on specific binding between a target analyte and a corresponding binding molecule to form a complex that can be readily detected. Examples of such complexes are receptor-ligand interactions such as an antigen-antibody interaction. Nucleic acids may be detected by hybridizing to substantially complementary nucleic acid sequences.

Multiplexed analyte detection, simultaneously performing different assays on the same sample or multiple samples, is on the rise. Examples of multiplexed analyte detection assays include DNA and protein chips and bead based assays. However, these methods can prove unsatisfactory in many applications.

Accordingly, there is a need in the art for compositions and methods for improving the sensitivity, speed and simplicity of analyte detection, and especially for such compositions and methods that are readily adaptable for detecting a wide variety of analytes including multiplexed analyte detection. The instant disclosure provides methods and compositions that meet these and other needs.

BRIEF SUMMARY OF THE INVENTION

Disclosed herein are methods and compositions for the detection of one or more target analyte(s) in one or more samples.

Accordingly, in some embodiments methods for detecting an analyte or analytes in one or more sample(s) are provided. The methods encompass providing a solid support with an addressable marker and an associated ligand, contacting the solid substrate to a sample, thereby forming a contacted solid support, associating the contacted solid support with a FET array and detecting the electrical properties of the FET array and thereby detecting an analyte or analytes in one or more samples. In other embodiments, the sample encompasses a second addressable marker.

In other embodiments, the methods encompass providing a solid support with a first addressable marker and an associated ligand, contacting the solid support with one or more sample(s), thereby forming a first contacted solid support, contacting the first contacted solid support with a selection moiety, thereby forming a second contacted solid support, applying the second contacted solid support to a FET array, detecting the electrical properties of the FET array and thereby detecting the analyte or analytes in one or more samples.

In some embodiments, the selection moiety encompasses a label, wherein the label is capable of creating an electrical charge change upon application of a condition. In some embodiments, the condition is a wavelength of light. In other embodiments, the condition is a substrate.

In some embodiments, a composition is provided encompassing a solid support, a ligand, an addressable marker and a filed effect transistor, wherein the ligand and the addressable marker are associated with the solid support. In some embodiments, the ligand is a protein. In some embodiments, the ligand is a human leukocyte antigen. In some embodiments, the ligand is an antibody. In other embodiments, the ligand is streptavidin.

In other embodiments, the composition encompasses a solid support, a ligand, a first addressable marker, a selection moiety, a second addressable marker and a FET, wherein the ligand and the first addressable marker are associated with the solid support.

These and other embodiments are described in more detail below.

BRIEF DESCRIPTION OF THE DRAWINGS

In the drawings, like reference characters generally refer to the same parts throughout the different views. Also, the drawings are not necessarily to scale, emphasis instead being placed upon generally illustrating the various concepts discussed herein.

Figure 1:
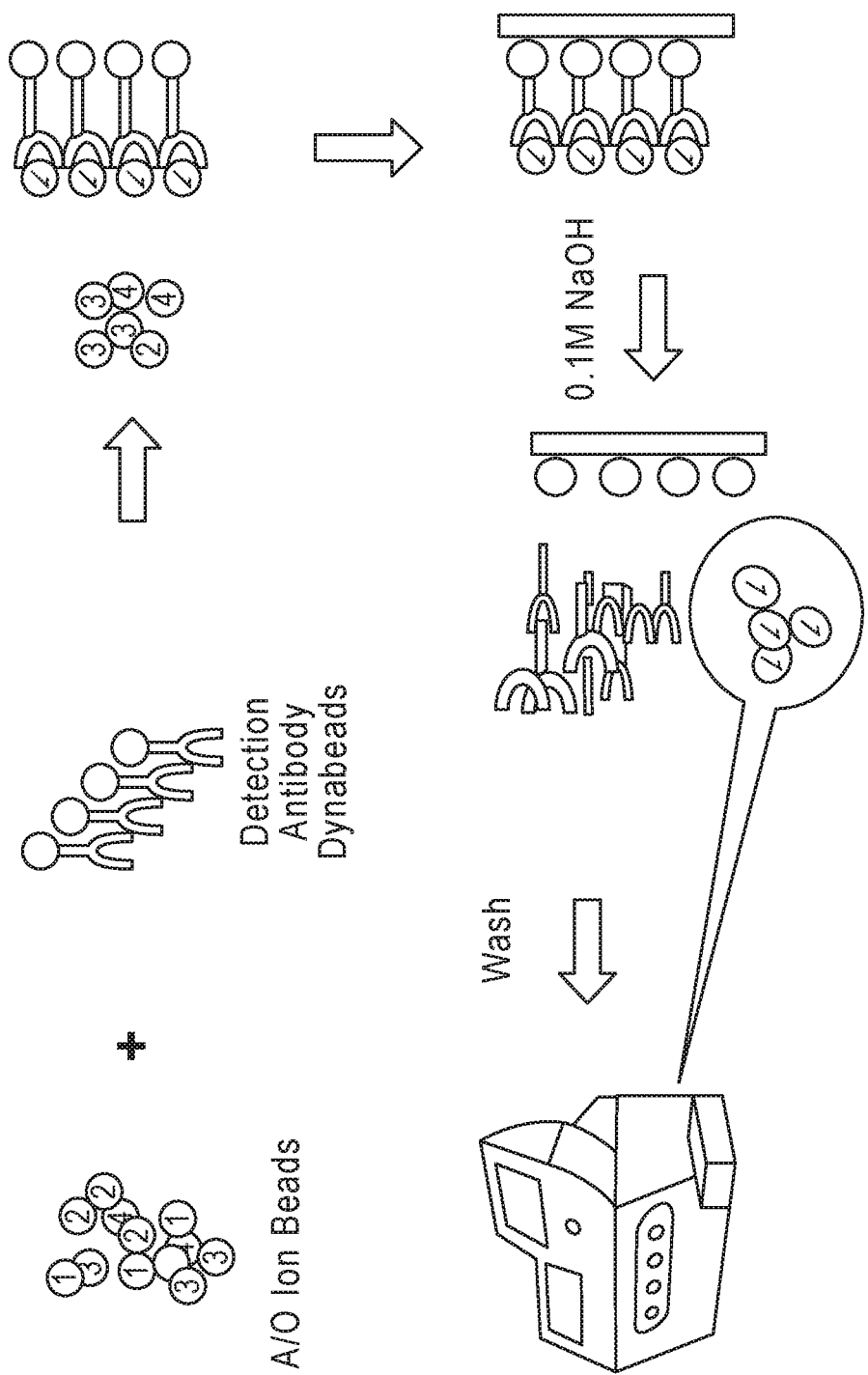
FIG. 1 shows a schematic representation of analyte detection using a Field Effect Transistor (FET). In this representation, a solid support "ion beads" is conjugated with one of four different addressable makers and four ligands. Each addressable marker here is an oligonucleotide and the oligonucleotide serves as an identifier for a particular ligand. In this representation the solid support is contacted with a selection moiety. The selection moiety here is an antibody specific for one of the ligands conjugated to a magnetic bead. This is exposed to a magnetic field and solid supports bound by the selection moiety are separated from unbound solid supports. The solid supports are released from the selection moiety, in this instance by the addition of 0.1M NaOH and the released solid supports are applied to a FET. Here the FET is used to sequence the addressable marker.
Figure 2:
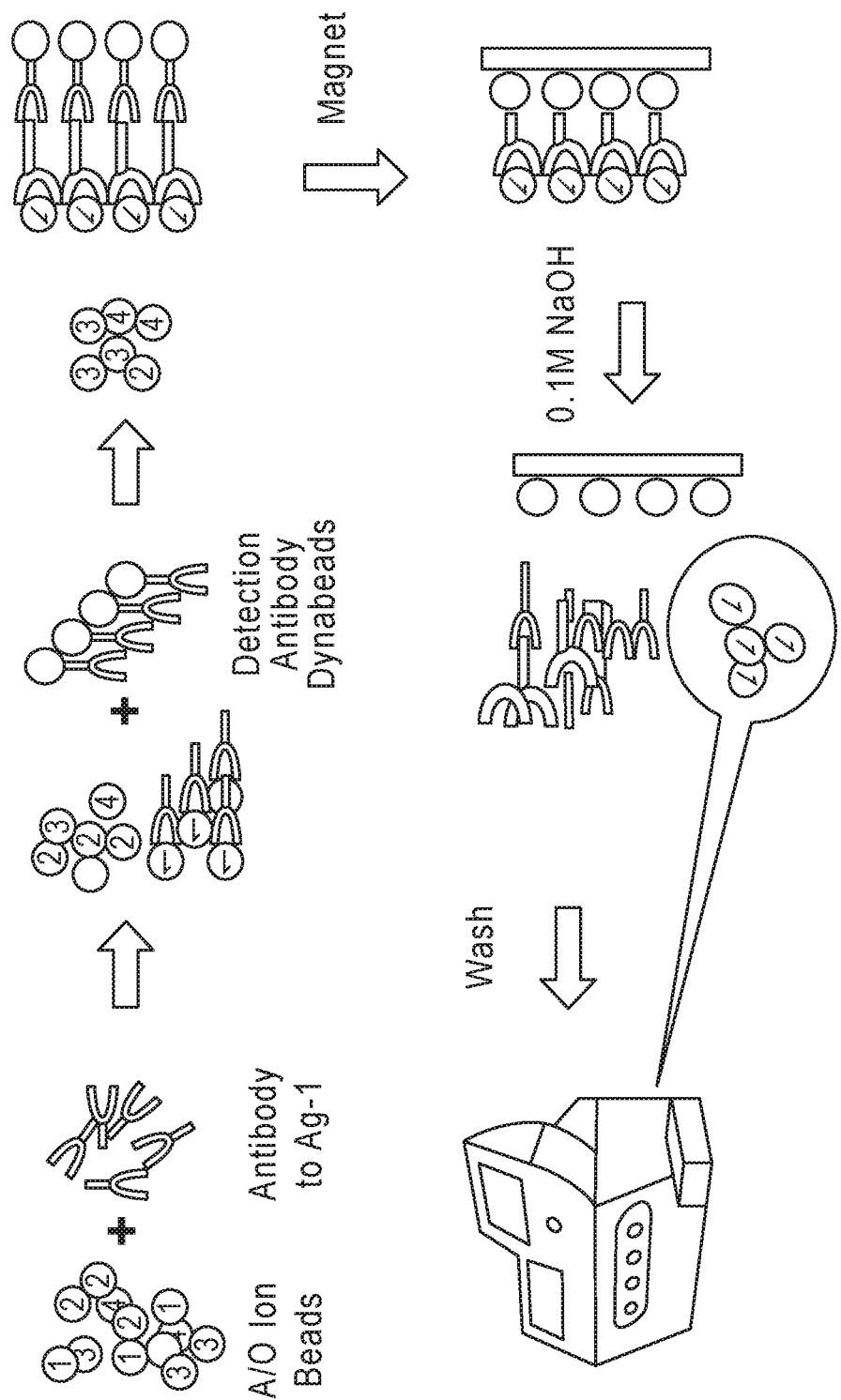
FIG. 2 shows another schematic representation of analyte detection using a FET. In this schema, a solid support "ion beads" is conjugated with one of four different addressable makers and four ligands. Each addressable marker here is an oligonucleotide and the oligonucleotide serves as an identifier for a particular ligand. In this representation the solid support is contacted with a sample containing an antibody analyte, which specifically recognizes one of the four ligands. This is then contacted with a selection moiety, identified in the schema as "detection antibody Dynabeads." The selection moiety specifically recognizes antibodies and therefore the antibody analyte. This is exposed to a magnetic field; thereby isolating the solid supports bound by the antibody analyte and in turn the selection moiety away from unbound solid supports. The solid supports are released from the selection moiety, in this instance by the addition of 0.1M NaOH and the released solid supports are applied to a FET. Here the FET is used to sequence the addressable marker. The sequence of the addressable marker correlates to the ligand bound to the same solid support and thereby acts as a proxy for detection of binding by an analyte.

Like a MOSFET, the operation of an ISFET is based on the modulation of charge concentration caused by a MOS (Metal-Oxide-Semiconductor) capacitance constituted by the polysilicon gate 64, the gate oxide 65 and the region 60 of the n-type well 54 between the source and the drain.

When a negative voltage is applied across the gate and source regions ($V_{GS}$<0 Volts), a "p-channel" 63 is created at the interface of the region 60 and the gate oxide 65 by depleting this area of electrons. This p-channel 63 extends between the source and the drain, and electric current is conducted through the p-channel when the gate-source potential V.sub.GS is negative enough to attract holes from the source into the channel. The gate-source potential at which the channel 63 begins to conduct current is referred to as the transistor's threshold voltage $V_{TH}$ (the transistor conducts when $V_{GS}$ has an absolute value greater than the threshold voltage $V_{TH}$). The source is so named because it is the source of the charge carriers (holes for a p-channel) that flow through the channel 63; similarly, the drain is where the charge carriers leave the channel 63.

Figure 10:
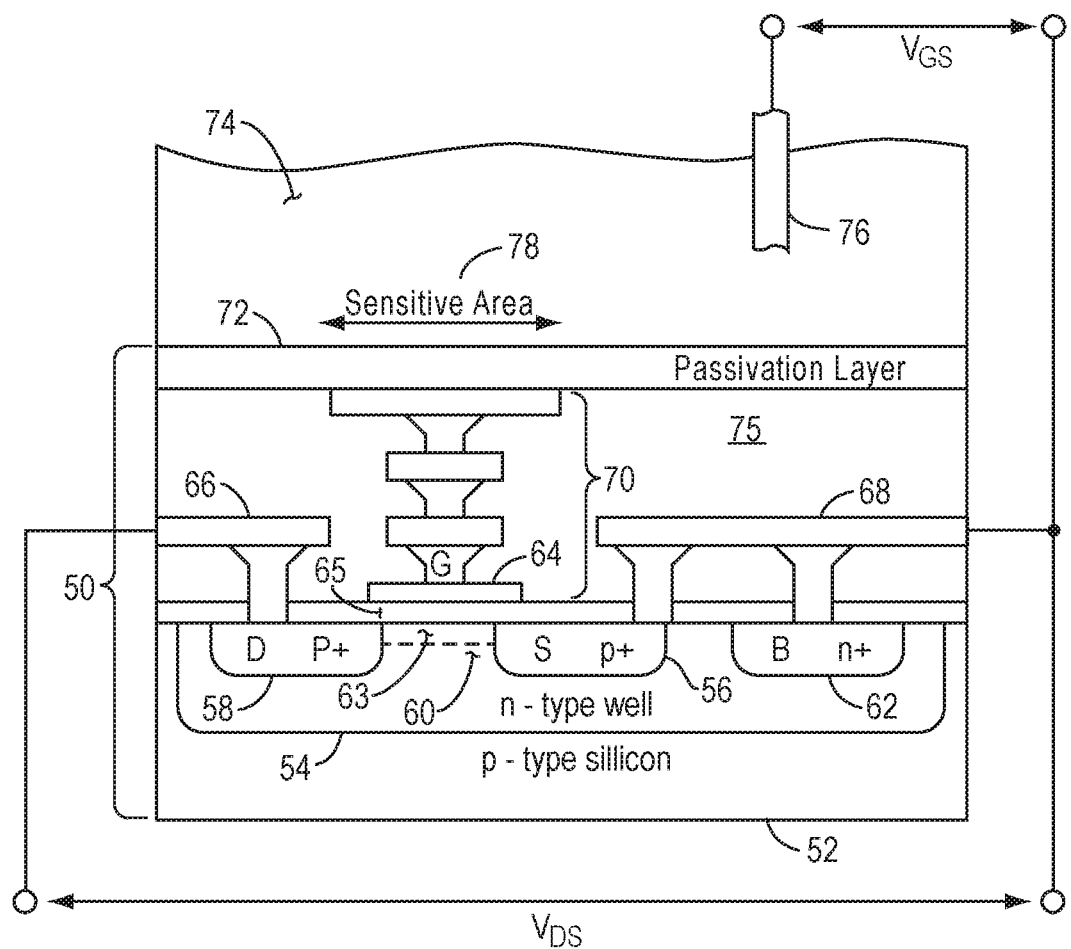
FIG. 10 shows a cross-section of a p-type (p-channel) ISFET 50 fabricated using a conventional CMOS (Complimentary Metal Oxide Semiconductor) process. However, biCMOS (i.e., bipolar and CMOS) processing may also be used, such as a process that would include a PMOS FET array with bipolar structures on the periphery. Taking the CMOS example, P-type ISFET fabrication is based on a p-type silicon substrate 52, in which an n-type well 54 forming a transistor "body" is formed. Highly doped p-type (p+) regions S and D, constituting a source 56 and a drain 58 of the ISFET, are formed within the n-type well 54. A highly doped n-type (n+) region B is also formed within the n-type well to provide a conductive body (or "bulk") connection 62 to the n-type well. An oxide layer 65 is disposed above the source, drain and body connection regions, through which openings are made to provide electrical connections (via electrical conductors) to these regions; for example, metal contact 66 serves as a conductor to provide an electrical connection to the drain 58, and metal contact 68 serves as a conductor to provide a common connection to the source 56 and n-type well 54, via the highly conductive body connection 62. A polysilicon gate 64 is formed above the oxide layer at a location above a region 60 of the n-type well 54, between the source 56 and the drain 58. Because it is disposed between the polysilicon gate 64 and the transistor body (i.e., the n-type well), the oxide layer 65 often is referred to as the "gate oxide."

In the ISFET 50 of FIG. 10, the n-type well 54 (transistor body), via the body connection 62, is forced to be biased at a same potential as the source 56 (i.e., $V_{SB}$=0 Volts), as seen by the metal contact 68 connected to both the source 56 and the body connection 62. This connection prevents forward biasing of the p+ source region and the n-type well, and thereby facilitates confinement of charge carriers to the area of the region 60 in which the channel 63 may be formed. Any potential difference between the source 56 and the body/n-type well 54 (a non-zero source-to-body voltage $V_{SB}$) affects the threshold voltage $V_{TH}$ of the ISFET according to a nonlinear relationship, and is commonly referred to as the "body effect," which in many applications is undesirable.

As also shown in FIG. 10, the polysilicon gate 64 of the ISFET 50 is coupled to multiple metal layers disposed within one or more additional oxide layers 75 disposed above the gate oxide 65 to form a "floating gate" structure 70. The floating gate structure is so named because it is electrically isolated from other conductors associated with the ISFET; namely, it is sandwiched between the gate oxide 65 and a passivation layer 72. In the ISFET 50, the passivation layer 72 constitutes an ion-sensitive membrane that gives rise to the ion-sensitivity of the device; i.e., the presence of—ions 74 (i.e., a solution containing analytes (including ions) of interest or being tested for the presence of analytes of interest) in contact with the passivation layer 72, particularly in a sensitive area 78 above the floating gate structure 70, alters the electrical characteristics of the ISFET so as to modulate a current flowing through the p-channel 63 between the source 56 and the drain 58. The passivation layer 72 may comprise any one of a variety of different materials to facilitate sensitivity to particular ions; for example, passivation layers comprising silicon nitride or silicon oxynitride, as well as metal oxides such as silicon, aluminum or tantalum oxides, generally provide sensitivity to hydrogen ion concentration (pH) in the analyte solution 74, whereas passivation layers comprising polyvinyl chloride containing valinomycin provide sensitivity to potassium ion concentration in the medium 74. Materials suitable for passivation layers and sensitive to other ions such as sodium, silver, iron, bromine, iodine, calcium, and nitrate, for example, are known.

With respect to ion sensitivity, an electric potential difference, commonly referred to as a "surface potential," arises at the solid/liquid interface of the passivation layer 72 and the analyte solution 74 as a function of the ion concentration in the sensitive area 78 due to a chemical reaction (e.g., usually involving the dissociation of oxide surface groups by the ions in the analyte solution 74 in proximity to the sensitive area 78). This surface potential in turn affects the threshold voltage $V_{TH}$ of the ISFET; thus, it is the threshold voltage $V_{TH}$ of the ISFET that varies with changes in ion concentration in the medium 74 in proximity to the sensitive area 78. Iodine, calcium, and nitrate, for example, are known.

DETAILED DESCRIPTION

The detection of various target analytes or molecules is an important tool for a variety of applications including diagnostic medicine, molecular biology research and environmental sciences. While methods for detecting different analytes have evolved, the ability to detect numerous analytes in a single sample or multiple samples has proven difficult.

The present disclosure is directed to the detection of an analyte or numerous analytes in one or more sample(s) by a field-effect transistor (FET).

"Analyte" or "analytes" refers to any molecule whose presence is measured. An analyte can be any molecule for which a detectable probe or assay exists or can be produced. For example, an analyte can be a macromolecule, such as a nucleic acid, polypeptide, carbohydrate, a small organic or inorganic compound, or an element, for example, gold, iron or lead. An analyte can be part of a sample that contains other components or can be the sole or major component of the sample. Therefore, an analyte can be a component of a whole cell or tissue, a cell or tissue extract, a fractionated lysate thereof or a substantially purified molecule.

In some embodiments, the target analyte is a polypeptide. "Polypeptide" and "protein" are used interchangeably to refer to a polymer of amino acid residues linked by a peptide bond. The polymer can be linear or branched and can include modified amino acids, and/or may be interrupted by non-amino acids. Polypeptides can occur as single chains or associated chains.

Antibodies are polypeptides which have received particular attention, since the presence of antibodies with certain specificities are hallmarks of disease, such as autoimmune disorders, and in terms of tissue transplantation, the risk of tissue rejection.

Accordingly, in some embodiments, a method for detecting the presence of an antibody in a sample is provided.

In some embodiments, a method for detecting an antibody encompasses contacting a ligand bound solid support to a sample, thereby forming a contacted solid support, applying the contacted solid support to a FET and detecting the electrical properties of the FET and thereby detecting the presence an antibody.

In some embodiments, a method for detecting an antibody in a sample encompasses contacting a ligand bound solid support with a sample, contacting the ligand bound solid support with a selection moiety, wherein the selection moiety binds the solid support in the presence of an antibody with specificity for the ligand, dissociating the solid support from the selection moiety, applying the solid support, with or without the ligand, to a FET and detecting the electrical properties of the FET and thereby detecting the presence an antibody.

An "antibody" or "antibodies" refers to a tetrameric protein composed of two identical pairs of polypeptide chains, each pair having one "light" chain (typically having a molecular weight of about 25 kDa) and one "heavy" chain (typically having a molecular weight of about 50-70 kDa).

Light chains are classified as kappa and lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

In some embodiments, the target analyte is an antibody heavy chain. In some embodiments, the target analyte is IgG. In other embodiments, the target analyte is IgM. In some embodiments, the target analyte is a human antibody heavy chain.

In some embodiments, the target analyte is an antibody light chain. In some embodiments, the target analyte is a kappa light chain. In some embodiments, the target analyte is a lambda light chain. In other embodiments, the target analyte is a human antibody light chain.

Antibodies that specifically bind to the human leukocyte antigen (HLA) are of particular clinical relevance, especially with regards to transplantation and transplant rejection.

"Specifically binds" refers to the specific interaction of one of at least two different molecules for the others compared to substantially less recognition of other molecules. Specific binding is an interaction with a $K_D$ of at least about 0.1 mM, at least about 1 μM, at least about 0.1 μM or better, or 0.01 μM or better. Binding can be assessed using surface plasma resonance.

An antibody that specifically binds to or shows specific binding towards an epitope means that the antibody reacts or associates more frequently, more rapidly, with greater duration, and/or with greater affinity with the epitope than with alternative substances. As such, "specific binding" does not necessarily require (although it can include) exclusive binding; that is, binding to a single target. Generally, but not necessarily, reference to binding means specific binding.

Transplant rejection occurs when the immune system of the recipient of a transplant, particularly antibodies produced by the recipient, attacks the transplanted organ or tissue. The recipient's immune system recognizes the transplanted organ as foreign tissue and attempts to destroy it. Rejection also occurs when the transplanted organ contains the donor's lymphocytes or progenitor stem cells, which may generate an immune response to the recipient tissues such as in graft versus host disease.

Accordingly, in some embodiments, the analyte detected is an antibody or antibodies that specifically bind HLA; that is an anti-HLA antibody or antibodies.

Human Leukocyte Antigen

HLA is a human major histocompatibility complex (hMHC) which is a cell surface antigen generally associated with graft rejection. HLA genes are classified into class I, II and III loci. HLA-A, -B and -C genes are present in the HLA class I locus, and HLA-DR, DQ and DP genes are present in the HLA class II locus.

An HLA class I molecule consists of a 45-kDa glycoprotein (heavy chain) non-covalently associated with a 12-kDa polypeptide, β2-microglobulin (β2 m).

HLA class II molecules are heterodimers formed by noncovalent linkage of two glycosylated polypeptide chains referred to as alpha and beta chains. The α subunit is 33 kDa and the β subunit is 28 kDa, and both chains are transmembrane polypeptides that have the same overall structure. The invariable a chain is encoded by the DRA HLA gene and this chain binds various β chains encoded by the DRB HLA genes. In addition, the DP and Dq HLA gene families each have one gene that encodes an a chain and a β chain.

Class I and class II HLA molecules exhibit extensive polymorphism generated by systematic recombinatorial and point mutation events; as such, hundreds, if not thousands, of different HLA types exist throughout the world's population, resulting in a large immunological diversity.

Such extensive HLA diversity throughout the population results in tissue or organ transplant rejection between individuals.

It was demonstrated some time ago that the presence of antibodies to donor HLA is a major risk factor for immediate graft loss. Commonly, anti-HLA antibodies can arise as a result of transfusions, prior transplants and/or pregnancies. Because of this, patients awaiting a transplant are routinely tested for the presence of anti-HLA antibodies. Testing continues after transplantation, since the development of anti-HLA antibodies can be indicative of transplant rejection.

Accordingly, in some embodiments, a method for detecting the presence of an anti-HLA antibody in a sample is provided, the method encompassing preparing a panel of solid supports, wherein to each solid support is attached an addressable marker and at least one ligand, contacting the solid support to a sample, applying the contacted solid support to the FET, detecting the electrical properties of the FET and thereby detecting the presence of the anti-HLA antibody. The addressable marker is associated with a particular ligand.

A "ligand" or "ligands" refer to any molecule capable of specifically binding to an analyte. In some embodiments, the ligand is a protein. In some embodiments, the ligand is an HLA. In some embodiments, the ligand is a class I HLA. In other embodiments, the ligand is a class II HLA.

In other embodiments, the method encompasses further contacting the contacted solid support to a selection moiety, thereby forming a second contacted solid support, applying the second contacted solid support to the FET, detecting the electrical properties of the FET and thereby detecting the presence of the anti-HLA antibody.

"Selection moiety" refers to a moiety that specifically binds the analyte. For example, the selection moiety can be, without limitation, a polypeptide, for example, an antibody, a nucleic acid, for example, an apatmer, or a lectin. Often the selection moiety includes a solid support.

"Solid support" refers any surface to which molecules may be attached through either covalent or non-covalent bonds. This includes, but is not limited to, membranes, plastics, paramagnetic beads, charged paper, nylon, functionalized glass, Anopore™, germanium, silicon, PTFE, polystyrene, metal, metal alloy, gallium arsenide, gold and silver. Any other material known in the art that is capable of having functional groups such as amino, carboxyl, thiol or hydroxylincorporated on its surface, is also contemplated. Solid support includes surfaces with any topology, including, but not limited to, spherical surfaces, grooved surfaces, and cylindrical surfaces for example, columns. In some embodiments, the solid support is a polyacrylamide bead. In some embodiments, the solid support is a bead. In some embodiments, the solid support is a hydrogel bead. Examples of hydrogel beads are Dynal LP889 or M-280.

In some embodiments, the selection moiety encompasses an antibody attached to a bead. In some embodiments, the bead is ferromagnetic.

"Attached", "affixed", "associated", "conjugated", "connected", "coupled", "immobilized", "adsorbed", and "linked" are used interchangeably and encompass direct as well as indirect connection, attachment, linkage, or conjugation, which may be reversible or irreversible, unless the context clearly dictates otherwise.

In addition to the ligand, addressable markers can also be attached to a solid support.

An "addressable marker" is an example of a surrogate. In some embodiments the presence of an addressable marker is detected and thereby the presence or absence of the corresponding analyte can be determined. In some embodiments, the addressable marker is a nucleic acid and thus the presence or absence of the corresponding analyte is determined by detecting a nucleic acid, for example by sequencing, hybridization, and/or PCR. In other embodiments, the addressable marker is a polypeptide. In some embodiments, the addressable marker is an oligonucleotide.

In some embodiments, the addressable marker is a DNA barcode. A DNA barcode is a DNA sequence of base pairs used to identify the molecule to which it is associated, directly or indirectly. For example, the DNA barcode can be attached to a solid support to which a molecule of interest is also attached. The identity of the attached molecule of interest can be discerned by or from the associated DNA barcode.

DNA barcodes can be prepared by carefully considering the performance characteristics of the assays that will be used to detect the barcodes. The barcodes can then be synthesized using any of the many readily available DNA synthesis techniques. The DNA barcode is designed to have a sufficient length to provide identification. Accordingly, in some embodiment, the DNA barcode can contain at least 4 nucleotides, at least 5 nucleotides, at least 6 nucleotides, at least 7 nucleotides, at least 8 nucleotides, at least 9 nucleotides, at least 10 nucleotides, at least 11 nucleotides, at least 12 nucleotides or more on a single DNA strand. In some embodiments, the DNA bar code is from 4-100 nucleotides, 6-90 nucleotides, 8-80 nucleotides in length.

In some embodiments, a method for detecting one or more analytes in a sample is provided. "Sample" refers to anything that can contain an analyte. The sample can be a "biological sample," such as a biological fluid or a biological tissue. Examples of biological fluids include, without limitation, blood, plasma, serum, saliva, urine, sputum, cerebral spinal fluid, tears, mucus, amniotic fluid, or semen. Biological tissues are aggregates of cells. Examples of biological tissues include organs, tumors and lymph nodes.

A biological sample is typically obtained from a eukaryotic organism, most preferably a mammal such as a primate. A biological sample can be obtained from a human donor of tissue or cells intended for transplantation or a human donor of blood or blood derivatives intended for transfusion. The biological sample may be obtained from a healthy bone marrow donor. The biological sample can also be obtained from a human subject that is an intended recipient of a transplant or transfusion, or the human subject that is donating the tissue or organ intended for transplantation or transfusion. Alternatively, the biological sample may be obtained directly from tissues or cells that are intended for transplantation in a human recipient. In addition, the biological sample may be obtained from blood or blood derivatives that are intended for transfusion in a human recipient.

In some embodiments, methods for preparing a solid support, for detection by a FET are provided. In some embodiments, the methods for preparing a solid support for detection by a FET encompass incubating for a period of time the solid support with a ligand in a phosphate buffered saline (PBS) solution including some but less than 1×PBS; that is, 01.×, 0.2×, 0.3×, 0.4×, 0.5×, 0.6×, 0.7×, 0.8× or 0.9×PBS. A 1×PBS solution is a solution composed of 8 g of NaCl, 0.2 g of KCl, 1.44 g of $Na_2HPO_4$ and 0.24 g of $KH_2PO_4$ dissolved in $H_2O$ to a total volume of 1l. In some embodiments, the solid support and the ligand are incubated in about a 0.25×PBS solution.

In some embodiments, a method for preparing a solid support for detection by a FET is provided, wherein the solid support is a bead and the bead is incubated in the presence of some but less than 1×PBS; that is, 01.×, 0.2×, 0.3×, 0.4×, 0.5×, 0.6×, 0.7×, 0.8× or 0.9×PBS. In some embodiments, the bead is a hydrogel bead. In some embodiments, attached to the bead is an addressable marker. In some embodiments, the addressable marker is an oligonucleotide. In some embodiments, the oligonucleotide contains a DNA barcode.

In some embodiments are provided a method for preparing a bead, and in turn, an analyte, for detection by a FET, the method encompassing incubating a bead conjugated with an oligonucleotide with a ligand in a solution encompassing some but less than 1×PBS; that is, 01.×, 0.2×, 0.3×, 0.4×, 0.5×, 0.6×, 0.7×, 0.8× or 0.9×PBS. In some embodiments, the solution is about 0.25×PBS. In some embodiments, the oligonucleotide encompasses a DNA bar code.

In some embodiments, the method encompasses, conjugating a hydrogel bead with an oligonucleotide, removing unconjugated oligonucleotide, thereby forming an oligonucleotide conjugated hydrogel bead, contacting the oligonucleotide conjugated hydrogel bead with a ligand, wherein the ligand is a protein in the presence of some but less than 1×PBS, that is, 01.×, 0.2×, 0.3×, 0.4×, 0.5×, 0.6×, 0.7×, 0.8× or 0.9×PBS, and thereby binding ligand to the oligonucleotide conjugated hydrogel bead, removing unbound ligand and thereby forming a ligand bound oligonucleotide conjugated hydrogel bead, contacting the ligand bound oligonucleotide conjugated hydrogel bead with a sample, removing excess sample, thereby forming a contacted ligand bound oligonucleotide conjugated hydrogel beads and applying the ligand bound oligonucleotide conjugated hydrogel bead to a FET. In some embodiments, the PBS is about 0.25×. In some embodiments, the PBS is 0.25×.

In some embodiments are provided a composition, the composition encompassing an oligonucleotide conjugated hydrogel bead and a ligand, wherein the oligonucleotide conjugated hydrogel bead and the ligand are in a solution encompassing some but less than 1×PBS; that is, 01.×, 0.2×, 0.3×, 0.4×, 0.5×, 0.6×, 0.7×, 0.8× or 0.9×PBS. In some embodiments, the solution is about 0.25×PBS. In some embodiments, the solution is 0.25×PBS. In some embodiments, the ligand is a protein. In some embodiments, the ligand is an HLA. In some embodiments the ligand is an antibody. In some embodiments, the ligand is streptavidin.

In some embodiments, a composition is provided encompassing an oligonucleotide and a bead, wherein the oligonucleotide is present between $1.5 \times 10^{-7}$M-$1.5 \times 10^{-9}$M and the number of beads present is between $1 \times 10^9$–$20 \times 10^9$. In some embodiments, the composition encompasses about $1.5 \times 10^{-8}$M oligonucleotide/$10 \times 10^9$ beads. In some embodiments, the oligonucleotide and bead composition further encompasses a solution of tributylamine and NMP.

In some embodiments, a composition is provided wherein between $1\text{-}10^{-8}$-$1 \times 10^{\times 10}$M protein is contacted to $1 \times 10^8$-$1 \times 10^{10}$ beads in a solution including some but less than 1×PBS; that is, 01.×, 0.2×, 0.3×, 0.4×, 0.5×, 0.6×, 0.7×, 0.8× or 0.9×PBS. In some embodiments, the PBS solution is about 0.25×PBS. In other embodiments, the PBS is 0.25×PBS.

These compositions and methods are applied to detection by field effect transistor. The addressable label, when in the form of an oligonucleotide, is identified by nucleic acid sequence analysis by detection of electrical change registered by a FET, when the nucleic acid is in the presence of polymerase and nucleotides.

The sequence determined correlates with the ligand, and in turn, the analyte that binds that specifically binds that ligand.

Field Effect Transistor

A Field Effect Transistor ("FETs") is a transistor that relies on an electric field to control the conductivity of a channel in a semiconductor material.

A FET has three terminals, which are referred to as the gate, drain and source. A voltage applied between the gate and the source terminals modulates the current between the source and drain terminals. A small change in the gate voltage can cause a large variation in the current from the source to the drain, thus enabling the FET to amplify signals.

FETs can be arranged into arrays. "Array" means an arrangement of locations on a substrate. The locations will generally be arranged in two-dimensional arrays, but other formats are possible. The number of locations can range from several to at least hundreds of thousands. The array pattern and density of locations can vary.

FETs can detect analytes by changes in charge; either by the detection of a charged analyte itself or by indirect generation or capture of charged species related to the presence of an analyte, for example the products of enzymatic reactions.

Because of the favorable characteristics, including sensitivity, speed and miniaturization potential of FETs, they are ideally suited for the detection of analyte in a sample. Accordingly, the methods and compositions encompass an apparatus that incorporates a FET.

In some embodiments, the addressable marker is an oligonucleotide and the oligonucleotide marker is sequenced by electrical charge changes detected by a FET.

Apparatus

In one aspect, the apparatus encompasses a sensor array and an array of sample-retaining regions on a surface thereof for retaining biological or chemical analytes delivered to the surface. In one embodiment, sample-retaining regions are integral with the sensor array and may have a wide variety of formats. Such regions may be defined by chemically reactive group on the surface of the sensor array, by binding compounds attached to the surface of the sensor array which are specific for predetermined analytes, by regions of hydrophobicity or hydrophilicity, or by spatial features such as microwells, cavities, weirs, dams, reservoirs, or the like.

As is exemplified below, analytes can be delivered to retaining regions of a sensor array in several ways. Where sensor arrays are employed as one-use sample characterization devices, such as with process, environmental or cellular monitoring, sample may be delivered by emersion, pipetting, pouring, or by other direct methods. Where sensor arrays are employed in sequential or cyclical reactions, reagents, wash solutions, and the like, can be delivered by a fluidic system under computer control.

For such latter applications, embodiments of the invention may further include a flow cell integrated with the sample-retaining regions and sensor array. As described more fully below, in one embodiment, such flow cell delivers sample fluids (including assay reactants, buffers, and the like) to sample-retaining regions under controlled conditions, which may include laminar flow, constant flow rate at each sample-retaining region, controlled temperature, minimization of bubbles or other flow disruptions, and the like. In one aspect, a flow cell of an apparatus of the invention comprises an inlet, an outlet, and an interior space, which when the flow cell is in communication with, for example sealingly bonded to, the arrays of sample-retaining regions and sensors forms a chamber that is closed except for the inlet and outlet. In some embodiments, the device is manufactured such that the flow cell and one or both the arrays are integral to each other. In other embodiments, the flow cell is sealingly bonded to the arrays. Either embodiment will prevent fluid leakage, which, among other possible hazards, would introduce electrical noise into the sample fluid. In one aspect, the apparatus of the invention includes a reference electrode in fluid contact with the sample fluid so that during operation an electrical potential difference is established between the reference electrode and the sensors of the array.

The apparatus can be adapted to detecting hydrogen ions, for example hydrogen ions released as part of, or result of, an enzymatic reaction. Nucleotide incorporation during DNA synthesis, as in DNA sequencing, can be detected by the release of a hydrogen ion, for example. Such a detection process is disclosed as a DNA sequencing method in Rothberg et al., U.S. patent publications 2009/0026082 and 2009/0127589.

Accordingly, in some embodiments the presence of the analyte is detected by nucleic acid sequencing, wherein the addressable marker or the first and second addressable markers, are nucleic acids. A positive sequencing reaction acts to detect the presence of the analyte and further can provide the identity of the ligand bound by the analyte. In some embodiments, the identity of the ligand bound and the sample can be provided.

In some embodiments, methods and compositions are employed to amplify the signal, for example, the number or concentration of ions, such as hydrogen ions produced.

It is important in these and various other aspects to detect as many released hydrogen ions as possible in order to achieve as high a signal (and/or a signal to noise ratio) as possible. Strategies for increasing the number of released protons that are ultimately detected by the FET surface include without limitation limiting interaction of released protons with reactive groups in the well, choosing a material from which to manufacture the well in the first instance that is relatively inert to protons, preventing released protons from exiting the well prior to detection at the FET, and increasing the copy number of templates per well (in order to amplify the signal from each nucleotide incorporation), among others.

In one aspect, the invention provides apparatus and devices for monitoring pH changes in polymerase extension reactions in an environment with no or limited buffering capacity. Examples of a reduced buffering environment include environments that lack pH buffering components in the sample fluid and/or reaction mixtures; environments in which surfaces of array components in contact with sample fluid and/or reaction mixtures have little or no buffering capacity; and environments in which pH changes on the order of 0.01, 0.05, 0.1, 0.2, 0.3, 0.4, 0.5, 0.6. 0.7, 0.8, 0.9 or 1.0 pH units are detectable for example via a FET.

Some instances of the invention employ an environment, including a reaction solution, that is minimally buffered, if at all. Buffering can be contributed by the components of the solution or by the solid supports in contact with such solution. A solution having no or low buffering capacity (or activity) is one in which changes in hydrogen ion concentration on the order of at least about +/−0.005 pH units, at least about +/−0.01, at least about +/−0.015, at least about +/−0.02, at least about +/−0.03, at least about +/−0.04, at least about +/−0.05, at least about +/−0.10, at least about +/−0.15, at least about +/−0.20, at least about +/−0.25, at least about +/−0.30, at least about +/−0.35, at least about +/−0.45, at least about +/−0.50, or more are detectable (e.g., using the FET sensors described herein).

The pH change per nucleotide incorporation is on the order of about 0.005. In some embodiments, the pH change per nucleotide incorporation is a decrease in pH. Reaction solutions that have no or low buffering capacity may contain no or very low concentrations of buffer, or may use weak buffers.

Figure 11:
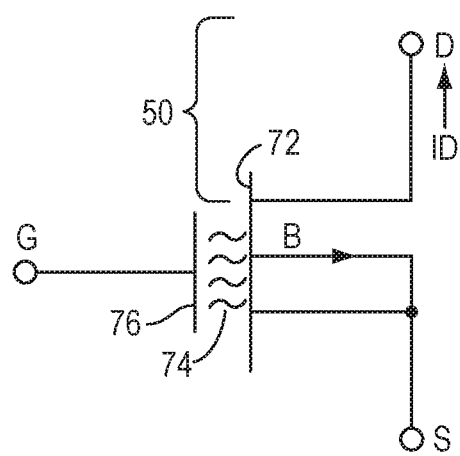
FIG. 11 shows an exemplary apparatus which is adapted for nucleic acid sequencing.

An exemplary apparatus is shown in FIG. 11 which is adapted for nucleic acid sequencing. In the discussion that follows, the FET sensors of the array are described for purposes of illustration as ion-sensitive field effect transistor (ISFETs) configured for sensitivity to static and/or dynamic ion concentration, including but not limited to hydrogen ion concentration. However, it should be appreciated that the present disclosure is not limited in this respect, and that in any of the embodiments discussed herein in which ISFETs are employed as an illustrative example, other types of FETs may be similarly employed in alternative embodiments, as discussed in further detail below. Similarly it should be appreciated that various aspects and embodiments of the invention may employ ISFETs as sensors yet detect one or more ionic species that are not hydrogen ions.

The system 1000 includes a semiconductor/microfluidics hybrid structure 300 comprising an ISFET sensor array 100 and a microfluidics flow cell 200. In one aspect, the flow cell 200 may comprise a number of wells (not shown in FIG. 11) disposed above corresponding sensors of the ISFET array 100. In another aspect, the flow cell 200 is configured to facilitate the sequencing of one or more identical template nucleic acids disposed in the flow cell via the controlled and ordered introduction to the flow cell of a number of sequencing reagents 272 (e.g., dATP, dCTP, dGTP, dTTP (generically referred to herein as dNTP), divalent cations such as but not limited to $Mg^{2+}$, wash solutions, and the like).

As illustrated in FIG. 11, the introduction of the sequencing reagents to the flow cell 200 may be accomplished via one or more valves 270 and one or more pumps 274 that are controlled by a computer 260. A number of techniques may be used to admit (i.e., introduce) the various processing materials (i.e., solutions, samples, reaction reagents, wash solutions, and the like) into the wells of such a flow cell. As illustrated in FIG. 10, reagents including dNTP may be admitted to the flow cell (e.g., via the computer controlled valve 270 and pumps 274) from which they diffuse into the wells, or reagents may be added to the flow cell by other means such as an ink jet. In yet another example, the flow cell 200 may not contain any wells, and diffusion properties of the reagents may be exploited to limit cross-talk between respective sensors of the ISFET array 100, or nucleic acids may be immobilized on the surfaces of sensors of the ISFET array 100.

The flow cell 200 in the system of FIG. 11 can be configured in a variety of manners to provide one or more analytes (or one or more reaction solutions) in proximity to the ISFET array 100. For example, a template nucleic acid may be directly attached or applied in suitable proximity to one or more pixels of the sensor array 100, or in or on a support material (e.g., one or more "beads") located above the sensor array but within the reaction chambers, or on the sensor surface itself. Processing reagents (e.g., enzymes such as polymerases) can also be placed on the sensors directly, or on one or more solid supports (e.g., they may be bound to the capture beads or to other beads) in proximity to the sensors, or they may be in solution and free-flowing. It is to be understood that the device may be used without wells.

In the system 1000 of FIG. 10, according to one embodiment the ISFET sensor array 100 monitors ionic species, and in particular, changes in the levels/amounts and/or concentration of ionic species, including hydrogen ions. In important embodiments, the species are those that result from a nucleic acid synthesis or sequencing reaction.

Via an array controller 250 (also under operation of the computer 260), the ISFET array may be controlled so as to acquire data (e.g., output signals of respective ISFETs of the array) relating to analyte detection and/or measurements, and collected data may be processed by the computer 260 to yield meaningful information associated with the processing (including sequencing) of the template nucleic acid.

With respect to the ISFET array 100 of the system 1000 shown in FIG. 10, in one embodiment the array 100 is implemented as an integrated circuit designed and fabricated using standard CMOS processes (e.g., 0.35 micrometer process, 0.18 micrometer process), comprising all the sensors and electronics needed to monitor/measure one or more analytes and/or reactions. With reference again to FIG. 10, one or more reference electrodes 76 to be employed in connection with the ISFET array 100 may be placed in the flow cell 200 (e.g., disposed in "unused" wells of the flow cell) or otherwise exposed to a reference (e.g., one or more of the sequencing reagents 172) to establish a baseline against which changes in analyte concentration proximate to respective ISFETs of the array 100 are compared. The reference electrode(s) 76 may be electrically coupled to the array 100, the array controller 250 or directly to the computer 260 to facilitate analyte measurements based on voltage signals obtained from the array 100; in some implementations, the reference electrode(s) may be coupled to an electric ground or other predetermined potential, or the reference electrode voltage may be measured with respect to ground, to establish an electric reference for ISFET output signal measurements, as discussed further below.

More generally, a FET array according to various embodiments of the present disclosure may be configured for sensitivity to any one or more of a variety of analytes. In one embodiment, one or more FETs of an array may be particularly configured for sensitivity to one or more analytes and/or one or more binding events, and in other embodiments different FETs of a given array may be configured for sensitivity to different analytes. For example, in one embodiment, one or more sensors (pixels) of the array may include a first type of FET configured to be sensitive to a first analyte, and one or more other sensors of the array may include a second type of FET configured to be sensitive to a second analyte different from the first analyte. In one exemplary implementation, both a first and a second analyte may indicate a particular reaction such as for example nucleotide incorporation in a sequencing-by-synthesis method. Of course, it should be appreciated that more than two different types of chemFETs may be employed in any given array to detect and/or measure different types of analytes and/or other reactions. In general, it should be appreciated in any of the embodiments of sensor arrays discussed herein that a given sensor array may be "homogeneous" and include FETs of substantially similar or identical types to detect and/or measure a same type of analyte (e.g., hydrogen ions), or a sensor array may be "heterogeneous" and include chemFETs of different types to detect and/or measure different analytes.

In other aspects of the system shown in FIG. 10, one or more array controllers 250 may be employed to operate the ISFET array 100 (e.g., selecting/enabling respective pixels of the array to obtain output signals representing analyte measurements). In various implementations, one or more components constituting one or more array controllers may be implemented together with pixel elements of the arrays themselves, on the same integrated circuit (IC) chip as the array but in a different portion of the IC chip, or off-chip. In connection with array control, analog-to-digital conversion of ISFET output signals may be performed by circuitry implemented on the same integrated circuit chip as the ISFET array, but located outside of the sensor array region (locating the analog to digital conversion circuitry outside of the sensor array region allows for smaller pitch and hence a larger number of sensors, as well as reduced noise). In various exemplary implementations discussed further below, analog-to-digital conversion can be 4-bit, 8-bit, 12-bit, 16-bit or other bit resolutions depending on the signal dynamic range required.

In general, data may be removed from the array in serial or parallel or some combination thereof. On-chip controllers (or sense amplifiers) can control the entire chip or some portion of the chip. Thus, the chip controllers or signal amplifiers may be replicated as necessary according to the demands of the application. The array may, but need not be, uniform. For instance, if signal processing or some other constraint requires instead of one large array multiple smaller arrays, each with its own sense amplifiers or controller logic.

Having provided a general overview of the role of a FET (e.g., ISFET) array 100 in an exemplary system 1000 for measuring one or more analytes, following below are more detailed descriptions of exemplary chemFET arrays according to various inventive embodiments of the present disclosure that may be employed in a variety of applications. Again, for purposes of illustration, FET arrays according to the present disclosure are discussed below using the particular example of an ISFET array, but other types of ETs may be employed in alternative embodiments. Also, again, for purposes of illustration, FET arrays are discussed in the context of nucleic acid sequencing applications, however, the invention is not so limited and rather contemplates a variety of applications for the chemFET arrays described herein.

As discussed elsewhere, for many uses, such as in DNA sequencing, it is desirable to provide over the array of semiconductor sensors a corresponding array of microwells, each microwell being small enough preferably to receive only one analyte, in connection with which an underlying pixel in the array will provide a corresponding output signal.

The use of such a microwell array involves three stages of fabrication and preparation, each of which is discussed separately: (1) creating the array of microwells to result in a chip having a coat comprising a microwell array layer; (2) mounting of the coated chip to a fluidic interface; and in the case of DNA sequencing, (3) loading DNA-loaded bead or beads into the wells. It will be understood, of course, that in other applications, beads may be unnecessary or beads having different characteristics may be employed.

The systems described herein can include an array of microfluidic reaction chambers integrated with a semiconductor comprising an array of FETs. In some embodiments, the invention encompasses such an array. The reaction chambers may, for example, be formed in a glass, dielectric, photodefineable or etchable material. The glass material may be silicon dioxide.

Various aspects or embodiments of the invention involve an apparatus comprising an array of FET sensors overlayed with an array of reaction chambers wherein the bottom of a reaction chamber is in contact with (or capacitively coupled to) a FET sensor. In some embodiments, each reaction chamber bottom is in contact with a FET sensor, and preferably with a separate FET sensor. In some embodiments, less than all reaction chamber bottoms are in contact with a FET sensor. In some embodiments, each sensor in the array is in contact with a reaction chamber. In other embodiments, less than all sensors are in contact with a reaction chamber. The sensor (and/or reaction chamber) array may be comprised of 2, 3, 4, 5, 6, 7, 8, 9, 10, 15, 20, 30, 40, 50, 60, 60, 80, 90, 100, 200, 300, 400, 500, 1000, $10^4$, $10^5$, $10^6$, $10^7$, $10^8$, or more FET sensors (and/or reaction chambers). As used herein, it is intended that an array that comprises, as an example, 256 sensors or reaction chambers will contain 256 or more (i.e., at least 256) sensors or reaction chambers.

Various aspects and embodiments of the invention involve sensors (and/or reaction chambers) within an array that are spaced apart from each other at a center-to-center distance or spacing (or "pitch", as the terms are used interchangeably herein) that is in the range of 1-50 microns, 1-40 microns, 1-30 microns, 1-20 microns, 1-10 microns, or 5-10 microns, including equal to or less than about 9 microns, or equal to or less than about 5.1 microns, or 1-5 microns including equal to or less than about 2.8 microns. The center-to-center distance between adjacent reaction chambers in a reaction chamber array may be about 1-9 microns, or about 2-9 microns, or about 1 microns, about 2 microns, about 3 microns, about 4 microns, about 5 microns, about 6 microns, about 7 microns, about 8 microns, or about 9 microns.

In some embodiments, the reaction chamber has a volume of equal to or less than about 1 picoliter (pL), including less than 0.5 pL, less than 0.1 pL, less than 0.05 pL, less than 0.01 pL, less than 0.005 pL.

The reaction chambers may have a square cross section, for example, at their base or bottom. Examples include an 8 μm by 8 μm cross section, a 4 μm by 4 μm cross section, or a 1.5 μm by 1.5 μm cross section. Alternatively, they may have a rectangular cross section, for example, at their base or bottom. Examples include an 8 μm by 12 μm cross section, a 4 μm by 6 μm cross section, or a 1.5 μm by 2.25 μm cross section.

In another exemplary implementation, the invention encompasses a system comprising at least one two-dimensional array of reaction chambers, wherein each reaction chamber is coupled to a chemically-sensitive field effect transistor ("chemFET") and each reaction chamber is no greater than 10 μm$^3$ (i.e., 1 pL) in volume. Preferably, each reaction chamber is no greater than 0.34 pL, and more preferably no greater than 0.096 pL or even 0.012 pL in volume. Preferably, the array has at least $10^2$, $10^3$, $10^4$, $10^5$, $10^6$, $10^7$, $10^8$, $10^9$, or more reaction chambers. The reaction chambers may be capacitively coupled to the chemFETs, and preferably are capacitively coupled to the chemFETs. Such systems may be used for high-throughput sequencing of nucleic acids.

In some embodiments, the reaction chamber array (or equivalently, microwell array) comprises $10^2$, $10^3$, $10^4$, $10^5$, $10^6$ or $10^7$ microwells or reaction chambers. In some embodiments, individual reaction chambers in the reaction chamber array are in contact with or capacitively coupled to at least one chemFET. In one embodiment, a reaction chamber of an array is in contact with or capacitively coupled to one chemFET or one ISFET. In some embodiments, the chemFET array may optionally comprise $10^2$, $10^3$, $10^4$, $10^5$, $10^6$ or $10^7$ chemFETs.

In these and in other aspects and embodiments, the chemFET or ISFET arrays may comprise 256 or more chemFETs or ISFETs. The chemFETs or ISFETs of such arrays may have a center-to-center spacing (between adjacent chemFETs or ISFETs) of 1-10 microns. In some embodiments, the center-to-center spacing is about 9 microns, about 8 microns, about 7 microns, about 6 microns, about 5 microns, about 4 microns, about 3 microns, about 2 microns or about 1 micron.

In particular embodiments, the center-to-center spacing is about 5.1 microns or about 2.8 microns.

In some embodiments, the bead is in a reaction chamber, and optionally the only bead in the reaction chamber. In some embodiments, the reaction chamber is in contact with or capacitively coupled to an ISFET. In some embodiments, the ISFET is in an ISFET array. In some embodiments, the bead has a diameter of less than 6 microns, less than 3 microns, or about 1 micron. The bead may have a diameter of about 1 micron up to about 7 microns, or about 1 micron up to about 3 microns.

In accordance with the invention, a dielectric layer on a gate of an ISFET is part of the ISFET. It is recognized that the charge in the reaction chamber builds up on one side of the dielectric and forms one plate of a capacitor and which has as its second plate the floating gate metal layer; thus, a reaction chamber is referred to as being capacitively coupled to the ISFET.

In some embodiments, the ISFET is in an ISFET array. The ISFET array may comprise $10^2$, $10^3$, $10^4$, $10^5$, $10^6$ or $10^7$ ISFETs.

In some embodiments, the template nucleic acid is in a reaction chamber in contact with or capacitively coupled to the ISFET. In some embodiments, the reaction chamber is in a reaction chamber array. In some embodiments, the reaction chamber array comprises $10^2$, $10^3$, $10^4$, $10^5$, $10^6$ or $10^7$ reaction chambers.

The microwells may vary in size between arrays. The size of these microwells may be described in terms of a width (or diameter) to height ratio. In some embodiments, this ratio is 1:1 to 1:1.5. The bead to well size (e.g., the bead diameter to well width, diameter, or height) is preferably in the range of 0.6-0.8.

The reaction well volume may range (between arrays, and preferably not within a single array) based on the well dimensions. This volume may be at or about 100 picoliter (pL), 90, 80, 70, 60, 50, 40, 30, 20, 10, or fewer pL. In important embodiments, the well volume is less than 1 pL, including equal to or less than 0.5 pL, equal to or less than 0.1 pL, equal to or less than 0.05 pL, equal to or less than 0.01 pL, equal to or less than 0.005 pL, or equal to or less than 0.001 pL. The volume may be 0.001 to 0.9 pL, 0.001 to 0.5 pL, 0.001 to 0.1 pL, 0.001 to 0.05 pL, or 0.005 to 0.05 pL. In particular embodiments, the well volume is 75 pL, 34 pL, 23 pL, 0.54 pL, 0.36 pL, 0.07 pL, 0.045 pL, 0.0024 pL, or 0.004 pL. In some embodiments, each reaction chamber is no greater than about 0.39 pL in volume and about 49 .mu.m.sup.2 surface aperture, and more preferably has an aperture no greater than about 16 .mu.m.sup.2 and volume no greater than about 0.064 pL.

Thus, it is to be understood that various aspects and embodiments of the invention relate generally to large scale FET arrays for measuring one or more analytes or for measuring charge bound to the chemFET surface. It will be appreciated that chemFETs and more particularly ISFETs may be used to detect analytes and/or charge. An ISFET, as discussed above, is a particular type of chemFET that is configured for ion detection such as hydrogen ion (or proton) detection. Other types of chemFETs contemplated by the present disclosure include enzyme FETs (EnFETs) which employ enzymes to detect analytes. It should be appreciated, however, that the present disclosure is not limited to ISFETs and EnFETs, but more generally relates to any FET that is configured for some type of chemical sensitivity. As used herein, chemical sensitivity broadly encompasses sensitivity to any molecule of interest, including without limitation organic, inorganic, naturally occurring, non-naturally occurring, chemical and biological compounds, such as ions, small molecules, polymers such as nucleic acids, proteins, peptides, polysaccharides, and the like.

In some embodiments, the invention encompasses a sequencing apparatus comprising a dielectric layer overlying a chemFET, the dielectric layer having a recess laterally centered atop the chemFET. Preferably, the dielectric layer is formed of silicon dioxide.

It should be understood that the readout at the chemFET may be current or voltage (and change thereof) and that any particular reference to either readout is intended for simplicity and not to the exclusion of the other readout. Therefore any reference in the following text to either current or voltage detection at the chemFET should be understood to contemplate and apply equally to the other readout as well. In important embodiments, the readout reflects a rapid, transient change in concentration of an analyte. The concentration of more than one analyte may be detected at different times. In some instances, such measurements are to be contrasted with methods that focus on steady state concentration measurements.

The process of using the assembly of an array of sensors on a chip combined with an array of microwells to sequence the DNA in a sample is referred to as an "experiment." Executing an experiment requires loading the wells with the DNA-bound beads and the flowing of several different fluid solutions (i.e., reagents and washes) across the wells. A fluid delivery system (e.g., valves, conduits, pressure source(s), etc.) coupled with a fluidic interface is needed which flows the various solutions across the wells in a controlled even flow with acceptably small dead volumes and small cross contamination between sequential solutions. Ideally, the fluidic interface to the chip (sometimes referred to as a "flow cell") would cause the fluid to reach all microwells at the same time. To maximize array speed, it is necessary that the array outputs be available at as close to the same time as possible. The ideal clearly is not possible, but it is desirable to minimize the differentials, or skews, of the arrival times of an introduced fluid, at the various wells, in order to maximize the overall speed of acquisition of all the signals from the array.

Increasing the number of templates or primers (i.e., copy number) results in a greater number of nucleotide incorporations per sensor and/or per reaction chamber, thereby leading to a higher signal and thus signal to noise ratio. Copy number can be increased for example by using templates that are concatemers (i.e., nucleic acids comprising multiple, tandemly arranged, copies of the nucleic acid to be sequenced), by increasing the number of nucleic acids on or in beads up to and including saturating such beads, and by attaching templates or primers to beads or to the sensor surface in ways that reduce steric hindrance and/or ensure template attachment (e.g., by covalently attaching templates), among other things. Concatemer templates may be immobilized on or in beads or on other solid supports such as the sensor surface, although in some embodiments concatemers templates may be present in a reaction chamber without immobilization. For example, the templates (or complexes comprising templates and primers) may be covalently or non-covalently attached to the chemFET surface and their sequencing may involve detection of released hydrogen ions and/or addition of negative charge to the chemFET surface upon a nucleotide incorporation event. The latter detection scheme may be performed in a buffered environment or solution (i.e., any changes in pH will not be detected by the chemFET and thus such changes will not interfere with detection of negative charge addition to the chemFET surface).

RCA or CCR amplification methods generate concatemers of template nucleic acids that comprise tens, hundreds, thousands or more tandemly arranged copies of the template. Such concatemers may still be referred to herein as template nucleic acids, although they may contain multiple copies of starting template nucleic acids. In some embodiments, they may also be referred to as amplified template nucleic acids. Alternatively, they may be referred to herein as comprising multiple copies of target nucleic acid fragment. Concatemers may contain 2, 3, 4, 5, 6, 7, 8, 9, 10, 20, 30, 40, 50, 60, 70, 80, 90, 100, 500, 1000, or more copies of the starting nucleic acid. They may contain $10$-$10^2$, $10^2$-$10^3$, $10^3$-$10^4$, $10^3$-$10^5$, or more copies of the starting nucleic acid. Concatemers generated using these or other methods (such as for example DNA nanoballs) can be used in the sequencing-by-synthesis methods described herein. The concatemers may be generated in vitro apart from the array and then placed into reaction chambers of the array or they may be generated in the reaction chambers. One or more inside walls of the reaction chamber may be treated to enhance attachment and retention of the concatemers, although this is not required. In some embodiments of the invention, if the concatemers are attached to an inside wall of the reaction chamber, such as the chemFET surface, then nucleotide incorporation at least in the context of a sequencing-by-synthesis reaction may be detected by a change in charge at the chemFET surface, as an alternative to or in addition to the detection of released hydrogen ions as discussed herein. If the concatemers are deposited onto a chemFET surface and/or into a reaction chamber, sequencing-by-synthesis can occur through detection of released hydrogen ions as discussed herein. The invention embraces the use of other approaches for generating concatemerized templates.

One such approach is a PCR described by Stemmer et al. in U.S. Pat. No. 5,834,252, and the description of this approach is incorporated by reference herein.

Important aspects of the invention contemplate sequencing a plurality of different template nucleic acids simultaneously. This may be accomplished using the sensor arrays described herein. In one embodiment, the sensor arrays are overlayed (and/or integral with) an array of microwells (or reaction chambers or wells, as those terms are used interchangeably herein), with the proviso that there be at least one sensor per microwell. Present in a plurality of microwells is a population of identical copies of a template nucleic acid. There is no requirement that any two microwells carry identical template nucleic acids, although in some instances such templates may share overlapping sequence. Thus, each microwell comprises a plurality of identical copies of a template nucleic acid, and the templates between microwells may be different.

It is to be understood therefore that the invention contemplates a sequencing apparatus for sequencing unlabeled nucleic acid acids, optionally using unlabeled nucleotides, without optical detection and comprising an array of at least 100 reaction chambers. In some embodiments, the array comprises $10^3$, $10^4$, $10^5$, $10^6$, $10^7$ or more reaction chambers. The pitch (or center-to-center distance between adjacent reaction chambers) is on the order of about 1-10 microns, including 1-9 microns, 1-8 microns, 1-7 microns, 1-6 microns, 1-5 microns, 1-4 microns, 1-3 microns, or 1-2 microns.

In various aspects and embodiments of the invention, the nucleic acid loaded beads, of which there may be tens, hundreds, thousands, or more, first enter the flow cell and then individual beads enter individual wells. The beads may enter the wells passively or otherwise. For example, the beads may enter the wells through gravity without any applied external force. The beads may enter the wells through an applied external force including but not limited to a magnetic force or a centrifugal force. In some embodiments, if an external force is applied, it is applied in a direction that is parallel to the well height/depth rather than transverse to the well height/depth, with the aim being to "capture" as many beads as possible. Preferably, the wells (or well arrays) are not agitated, as for example may occur through an applied external force that is perpendicular to the well height/depth. Moreover, once the wells are so loaded, they are not subjected to any other force that could dislodge the beads from the wells.

The Examples provide a brief description of an exemplary bead loading protocol in the context of magnetic beads. It is to be understood that a similar approach could be used to load other bead types. The protocol has been demonstrated to reduce the likelihood and incidence of trapped air in the wells of the flow chamber, uniformly distribute nucleic acid loaded beads in the totality of wells of the flow chamber, and avoid the presence and/or accumulation of excess beads in the flow chamber.

In various instances, the invention contemplates that each well in the flow chamber contain only one nucleic acid loaded bead. This is because the presence of two beads per well will yield unusable sequencing information derived from two different template nucleic acids.

As part of the sequencing reaction, a dNTP will be ligated to (or "incorporated into" as used herein) the 3' of the newly synthesized strand (or the 3' end of the sequencing primer in the case of the first incorporated dNTP) if its complementary nucleotide is present at that same location on the template nucleic acid. Incorporation of the introduced dNTP (and concomitant release of PPi) therefore indicates the identity of the corresponding nucleotide in the template nucleic acid. If no dNTP has been incorporated, no hydrogens are released and no signal is detected at the chemFET surface. One can therefore conclude that the complementary nucleotide was not present in the template at that location. If the introduced dNTP has been incorporated into the newly synthesized strand, then the chemFET will detect a signal. The signal intensity and/or area under the curve is a function of the number of nucleotides incorporated (for example, as may occur in a homopolymer stretch in the template. The result is that no sequence information is lost through the sequencing of a homopolymer stretch (e.g., poly A, poly T, poly C, or poly G) in the template.

All publications, patents, and patent applications mentioned in this specification are herein incorporated by reference to the same extent as if each individual publication, patent, or patent application was specifically and individually indicated to be incorporated by reference.

Other aspects and advantages of the present invention will be understood upon consideration of the following illustrative example.

EXAMPLES

Example 1: Activation of Hydrogel Beads

To activate the solid support for subsequent conjugation with oligonucleotides and protein, $1\times10^9$ hydrogel beads (Dynal LP889) was added to 1 ml. of N-methylpyyrolidone (NMP) and then subjected to centrifugation at 15,000 r.p.m., for 15 minutes at room temperature. Following this, the supernatant was removed and the hydrogel bead pellet was re-suspended in 1 ml. of "bis stock solution." The bis stock solution contained 41.4 µl of 469.5 mM Bis(NHS)PEG$_5$ (in NMP), 4.72 µl of 4.2M tributylamine and 954 µl of anhydrous NMP, which were mixed together using a vortex. The Bis(NHS)PEG$_5$ solution was prepared by dissolving 100 mg. of Bis(NHS)PEG$_5$ in 400 µl of anhydrous NMP to make a 375.6 mM solution, which was stored at −20° C.

Figure 3:
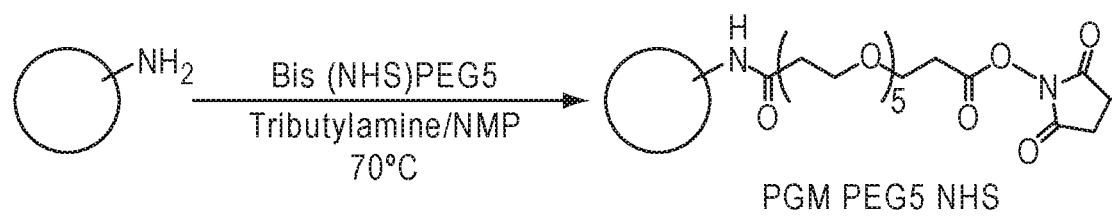
FIG. 3 shows a schematic representation of the addition of a PEG moiety to the solid support. The PEG moiety serves as the chemical linker that ultimately is used to connect a ligand and an addressable marker to the solid support. Often the ligand is a protein, such as HLA and the addressable marker is an oligonucleotide.

The hydrogel beads were incubated in the bis stock solution for 2 hours at 70° C. on a rotator, 950 r.p.m. Following the incubation, this mixture was cooled to room temperature and subjected to centrifugation at 15,000 r.p.m., for 15 minutes at room temperature. A schematic of this reaction is shown in FIG. 3.

Example 2: Coupling of Anti-human IgG Antibody to Dynabeads®

50 µl of Dynabeads® M-280 Streptavidin (Life Technologies, Carlsbad, Calif.) are added to a tube containing 1 ml of PBS/Tween® 0.05%, pH 7.0. The tube containing the Dynabeads® is placed on a magnet for 2 minutes, following this incubation, and while the tube is maintained on the magnet, the liquid is removed by aspiration. The tube containing the Dynabeads® is then removed from the magnet and washed. The Dynabeads® were subjected to two more additional magnetic aspiration/wash steps, followed by resuspending the finally washed beads in 275 µl of PBS. To this is added 25 µl of 0.5 mg/ml biotinylated anti-human IgG antibody in PBS, and incubated for 30 minutes at room temperature with gently rotation. The antibody treated beads were then applied to a magnet for 2-3 minutes, and the surrounding fluid aspirated off. The antibody coated Dynabeads® were washed 3-4 times in PBS containing 0.05% Tween®-20. The antibody coated beads were then re-suspended in PBS containing 0.1% casine.

Example 3: Analysis of the Conjugation of Oligonucleotides and Ligands to Hydrogel Beads At the outset the challenged faced was with coupling the oligonucleotides, ligands and hydrogel beads such that each would remain functional. It was unknown whether conditions could be found that would allow for conjugation of hydrogel beads with both nucleic acids (for example, oligonucleotides) and protein ligands (for example, HLA molecules, antibodies, and streptavidin), which would allow for sequencing of the nucleic acid and detection of the protein by a selection moiety (affinity reagent). The difficulty associated with conjugating nucleic acid and protein to beads for subsequent analysis was borne out by initial experiments.

In a first series of experiments, following the 2 hour incubation in bis stock solution and cooling described in Example 1, one of four oligonucleotide sequences (described below) was added to an aliquot of the activated hydrogel beads and incubated 20 minutes in 1× phosphate buffered saline (PBS, Fisher Catalog #BP399-500) at pH 8.0. After 20 minutes, one of four HLA proteins was added to an aliquot of hydrogel beads labeled with a particular oligonucleotide, and a further incubation for an additional 4 hours at room temperature was carried out. After this, the reaction mixture was washed and diluted with 1×PBS, pH 8.0 (50 µl, $1.8 \times 10^{-5}$M).

The resulting supernatant was removed. The pellet was then wash 3 times in 1 ml. of NMP, after which the pellet was resuspended in 250 µl of NMP resulting in a concentration of approximately $40 \times 10^6$ beads/µl.

The presence of the oligonucleotides on the hydrogel bead was detected using SYBR®Gold, while the presence of HLA protein on the solid support was detected using a fluorescent labeled antibody. The presence of HLA antigen on the hydrogel bead was established by staining beads with fluorescent antibody. To the bead suspension in pH 8.0 1×PBS buffer (100) ZyMax™ Goat anti-Human IgG (H+L) FITC conjugate solution in pH 8.0 1×PBS buffer was added (500, 0.1 mg/ml). The mixture was incubated for 15 min at RT, then was centrifuged to remove supernatant (10 min, 15,000 r.p.m.) and re-dispersed in pH 8.0 1×PBS buffer (1000). Centrifuge again to remove supernatant (10 min, 15,000 r.p.m.) and pellet was re-dispersed in annealing buffer (100 µl, Ion Torrent™ Catalog #603-1048-01). Beads were imaged by fluorescent microscopy and the presence of antigen was confirmed by control beads (pre-conjugation) treated the same way as conjugated beads and imaged by fluorescent microscopy.

The addition of one particular HLA molecule with a certain oligonucleotide allows for the identification of the analyte. Analyte detection in a sample here was carried out as follows. The solid supports with attached oligonucleotides and proteins (different HLA molecules) were pooled, 2 million beads of each oligonucleotide/HLA pair. The pooled beads are washed, and 200 µl of 1:10 diluted antibody (IHB072, 048, 077; Leiden University) are incubated together for 40 minutes at room temperature, with gentle rotation. After this incubation, unbound antibody is removed by washing. To the washed sample, 30 µl of anti-human IgG coupled Dynabeads® are added and incubated at room temperature for 40 minutes with gentle rotation. After this incubation, the reaction tube was subjected to a magnet field, and the supernatant removed. This step, magnet/wash was repeated and then the hydrogel beads were resuspended in 200 µl of Tris buffer pH8 (Ambio), 2 µl of 50 uM $CaCl_2$ (Sigma-Aldrich) and 1 µl of proteinase K (Sigma-aldrich P4850) were added. This reaction was then incubated for 1 hour at 50° C. with shaking, after which 1 µl of PMSF (Sigma-Aldrich, Cat #36978) was added and incubated for 15 minutes to inactivate the Proteinase K. This reaction was then subjected to centrifugation for 2 minutes and the supernatant was discarded. The pellet was re-suspended in newly prepared melt-down buffer (864 µl $H_2O$, 125 µl 1M NaOH, 10 µl 10% Tween®-20 (polysorbate 20), followed by an incubation at room temperature for 10 min with rotation. Following this incubation, the reaction was again subjected to centrifugation, the supernatant was removed and saved and the pelleted beads were washed with 200 µl annealing buffer from Ion Torrent 200 bp Sequencing kit. The protocol for the sequencing kit was then followed.

After extracting the FastQ file from Ion Torrent™ browser, the PGM® sequence data is subject in to Cobalt mapper software (in house developed software) for the barcode finding.

Results of several sequencing runs and conditions described in Example 3 are provided in Table 1.

TABLE 1

| | Panel beads | Pull Down Antibody | Detection Antibody | Total Reads | Expected Barcode |
|---|---|---|---|---|---|
| Assay1 | HIgG/HLA2 A11/HLA3 B07/HLA4 | IHB077 (A11) | Anti-hIgG Dynabeads M-280 | 17 | 71% |
| Assay2 | HIgG/HLA4 A23/HLA1 A11/HLA3 | IHB048 (A23) | Anti-hIgG Dynabeads M-280 | 159 | 57% |
| Assay3 | HIgG/HLA2 A23/HLA1 B07/HLA4 | IHB072(A23) | Anti-hIgG Dynabeads MyOne™ Streptavidin C1 | 11 | 45% |

While there was a correlation between predicted analyte and the oligonucleotide sequence, the number of reads, as a percentage of input beads, was extremely low. At this point, it was unknown whether any improvement could be realized since a hydrogel bead conjugated with both a protein and an oligonucleotide for subsequent analyte detection by sequencing, particularly sequencing by the detection of pH change had not previously been described, it was unknown at the outset what conditions could be used for conjugation.

Example 4: Titration of Oligonucleotide

It was observed in earlier experiments that the hydrogel beads conjugated with both oligonucleotide and proteins "clumped." The cause of this clumping was unknown. It was reasoned though that this clumping phenomena was a hinder to downstream analysis. Various conditions and concentrations of oligonucleotide were tested in the conjugation reaction.

The coupling reaction was accomplished as follows. A hydrogel bead stock ($1 \times 10^9$-$1 \times 10^{10}$ beads) was placed in a 2 ml. microcentrifuge tube and subjected to centrifugation for 15 minutes at 15,000 r.p.m., the supernatant was removed by pipette, and the pellet was resuspended in NMP. This process was repeated two more times. After this, 1 ml. of a Bis(NHS)$PEG_5$ stock solution was added to the beads, the microcentrifuge tube was vortex for approximately 10 seconds followed by brief centrifugation in order to pool the solution at the bottom of the microcentrifuge tube. The microcentrifuge tube was then incubated at 70° C. for 2 hour at 950 r.p.m. Following this incubation, the microcentrifuge tube was subjected to centrifugation at 15,000 r.p.m. for 15 minutes at room temperature to pellet the beads. The supernatant was removed from the resulting pellet with a pipette. The pellet was then washed three times in anhydrous NMP and resuspended to a final concentration of 40 million beads/µl.

Oligonucleotides were coupled to the activated hydrogel beads via a $PEG_5$-NHS linker. To accomplish this, oligonucleotides (described below) were dissolved in NMP and added to the activated hydrogel beads with $3.0\times10^{-8}$M tributylamine. This mixture was vortexed for 10 seconds, followed by brief centrifugation to pool the solution to the bottom of the microcentrifuge tube and incubated for 30 minutes at 60° C. at 950 r.p.m. Following this incubation, the microcentrifuge tube was subjected to centrifugation for 15 minutes at 15,000 r.p.m. The supernatant was then removed with a pipette.

The pellet was washed three times with 1 ml. anhydrous NMP and resuspended in a final volume of 500 µl. of anhydrous NMP.

Figure 4:
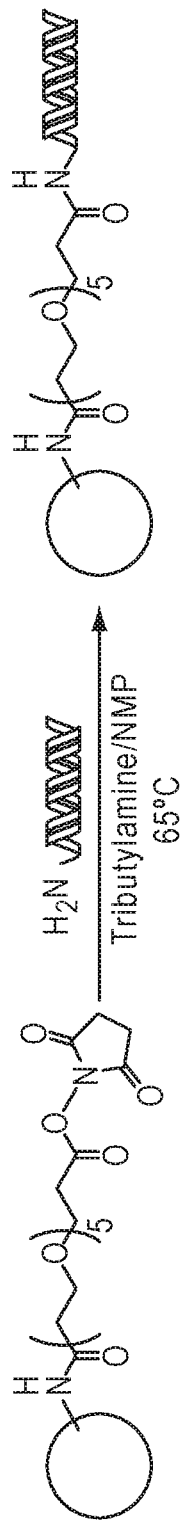
FIG. 4 shows a schematic representation of the addition of oligonucleotides to the slid supports via the PEG moiety and various concentrations of oligonucleotides used in conjugation experiments.

FIG. 4 depicts conditions used during the titration experiments.

Figure 5:
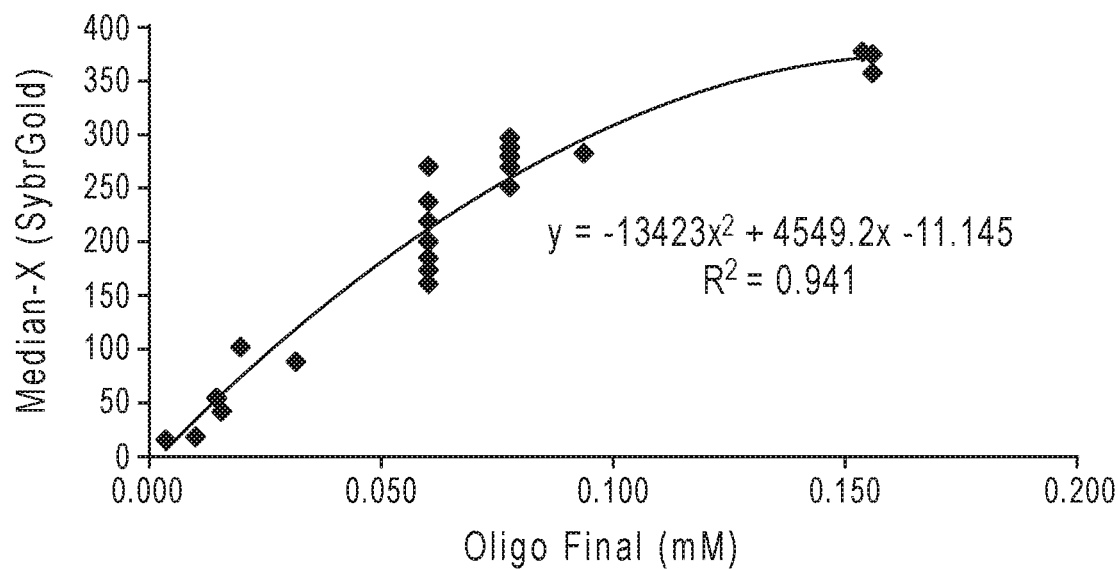
FIG. 5 shows a titration curve of oligonucleotide concentration versus SYBR®Gold signal intensity detected on a Guava flow cytometer.
Figure 6:
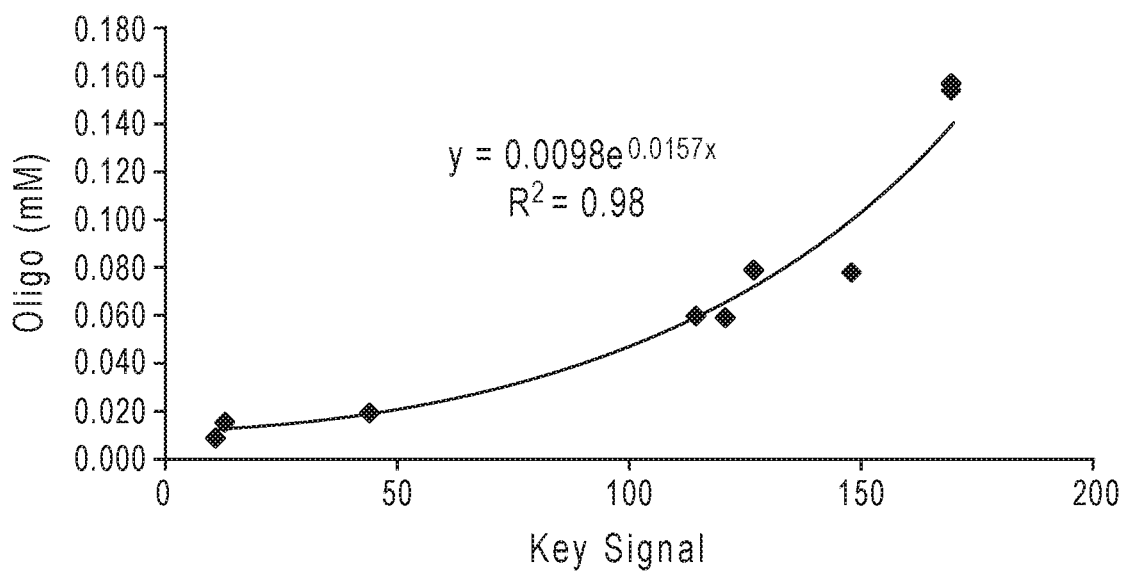
FIG. 6 shows a graph depicting the relationship between the detection of oligonucleotide sequence ("key signal") on a FET sensor as compared to the concentration of oligonucleotide used in solid support conjugation.

A titration curve of starting oligonucleotide concentration versus the level of SYBR® Gold staining is shown in FIG. 5. Nucleic sequencing data based on input oligonucleotide concentration is shown in FIG. 6. Contrary to expectations, relatively lower concentrations of input oligonucleotide were found to provide both favorable sequencing and protein conjugation characteristics.

All the oligonucleotides were 50 nucleotides in length. The sequences of the oligonucleotides were as follows:

SEQ ID NO.: 1:
CACGCTCATCGTTACCTTAGCTGAGTCGGAGACACGCAGGGATGAGATGG

SEQ ID NO.: 2:
CACGCTCATCGTTCTCCTTACTGAGTCGGAGACACGCAGGGATGAGATGG

SEQ ID NO.: 3:
CACGCTCATCGAATCCTCTTCTGAGTCGGAGACACGCAGGGATGAGATGG

SEQ ID NO.: 4:
CACGCTCATCGATCTTGGTACTGAGTCGGAGACACGCAGGGATGAGATGG

The 5' ends of each of these oligonucleotides were modified with a C12 spacer arm (amino (NH2-) modified C12). The bold nucleotides represent the barcodes, which identify each oligonucleotide.

Example 5: Titration of Protein Conjugation

To couple protein ligand to the oligonucleotide labeled hydrogel beads, the oligonucleotide labeled hydrogel beads are centrifuged for 15 minutes at 15,000 r.p.m. The supernatant was removed. The ligand was coupled to the oligonucleotide labeled hydrogel beads in a reaction mixture composed of 300 µl. of nuclease free water, PBS, pH 8.0, $1.8\times10^{-9}$M human IgG and $2.5\times10^6$/µl. oligonucleotide labeled hydrogel beads in a total volume of 400 µl. The mixture was briefly vortex to mix and then briefly centrifuged to pool the solution. This mixture was then incubated for 4 hours at 22° C. at 550 r.p.m. in order to conjugate the ligand, in this instance human IgG, to the oligonucleotide labeled hydrogel beads. Following this incubation, the mixture was centrifuged for 15 minutes at 15,000 r.p.m. The supernatant was removed by pipetting and the pellet was wash 2 times with PBS. For each wash, the pellet was re-suspended by pipetting and gentle vortexing, followed by centrifugation at 15,000 r.p.m. After the final wash, the pellet was resuspended in approximately 200 µl. of PBS.

Figure 7:
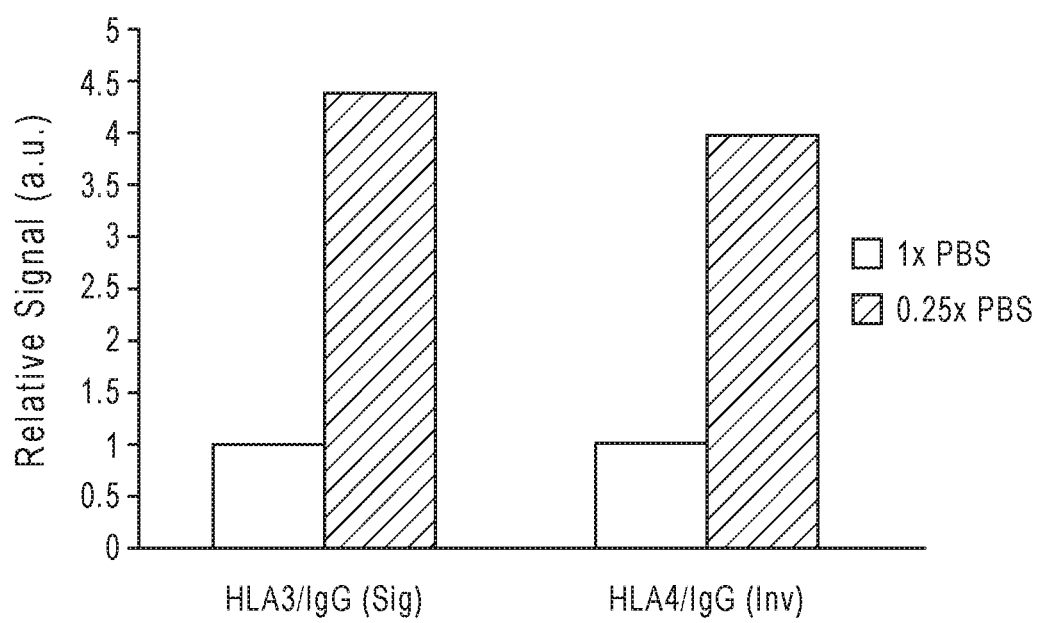
FIG. 7 shows a bar graph summarizing the influence of salt concentration during protein conjugation and sequence detection by FET. As depicted a better correlation between protein analyte and oligonucleotide sequence is found when the salt concentration is reduced from 1×PBS to 0.25×PBS during protein conjugation.

Even with lowered starting oligonucleotide concentrations, functional protein conjugation remained challenging. Protein conjugated beads were found to "clump," precluding downstream analysis. One possibility explored was the influence of salt concentrations. The influence of salt concentration on conjugated hydrogel bead clumping is shown in FIG. 7. In light of this data, in all instances in which PBS was used, the concentration of PBS was adjusted to 0.25×.

Example 6: Flow Cytometric Analysis of Conjugated of Oligonucleotide/Ligand Conjugated Hydrogel Beads ("Conjugated Beads")

The conjugated beads were assayed by flow cytometry to determine final bead concentration, to assess the level of bead clumping and determine the levels of oligonucleotide and ligand binding.

To determine final bead concentration, level of clumping and oligonucleotide conjugation, an aliquot of the conjugated beads was labeled with SYBR® Gold nucleic acid gel stain (Molecular Probes) and applied to a Guava® flow cytometer (Millipore) for analysis. Ideally, bead clumping should be minimized, with clumps of 4 of more beads as low as possible (<15%).

Figure 8:
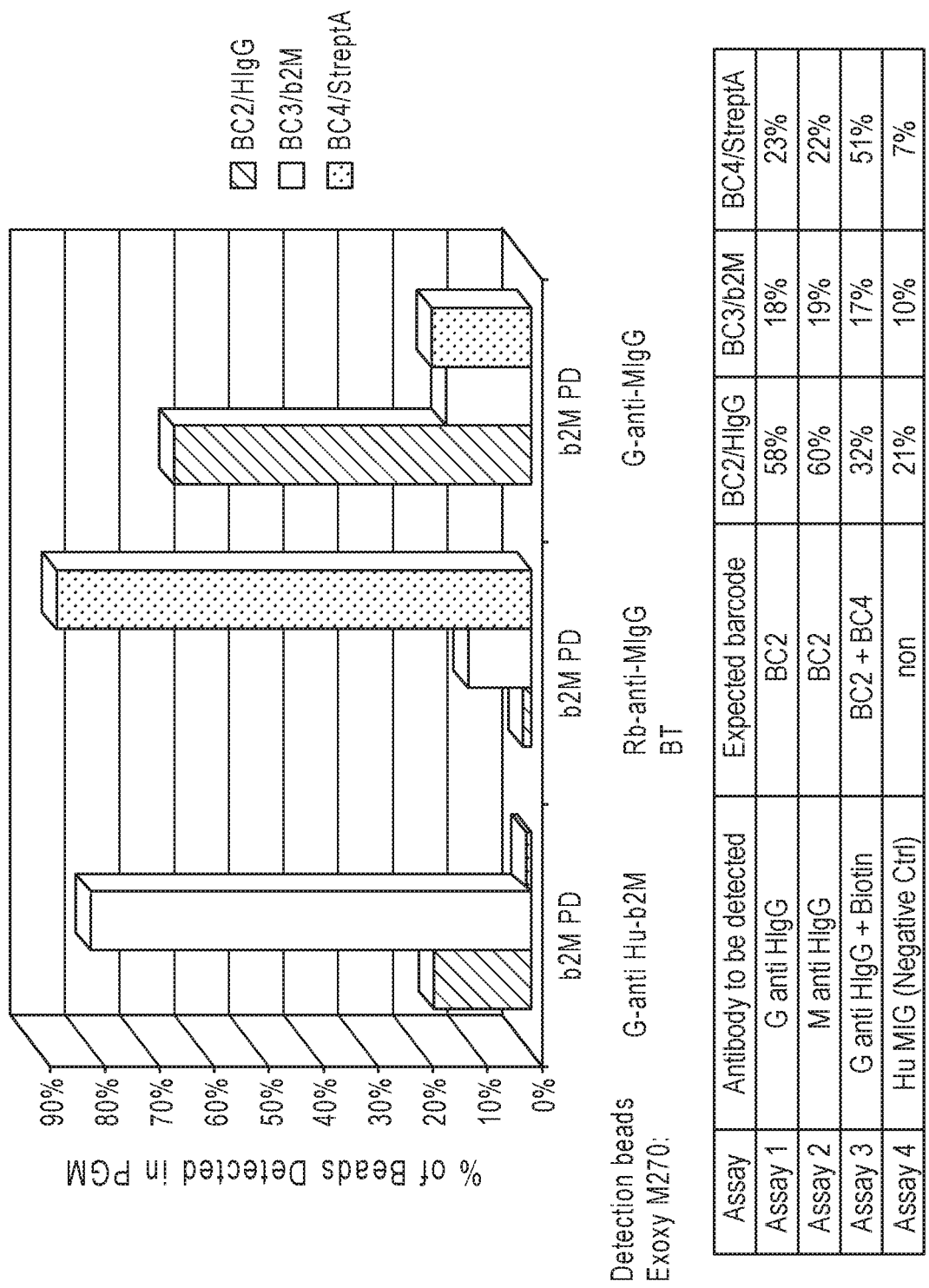
FIG. 8 shows a bar graph depicting the correlation between the percentage of beads sequenced to the expected protein. In all instances, there was a high correlation between the addressable marker (oligonucleotide sequence) and the protein conjugated to the same bead. The background level was less than 20%.

To determine the level of ligand conjugation, in this instance human IgG, between 1-10 µl. of conjugated beads were added to 400 µl. of sample dilution buffer (0.25×PBS, pH 7.4, 0.1% casein) in a 1.5 ml. low binding PCR tube. This was placed on a rotator for 30 minutes at room temperature in order to reduce possible non-specific binding by detection antibodies in the next step. Following this incubation, the conjugated beads are pelleted by centrifugation at 15,000 r.p.m., for 5 minutes at room temperature. 350 µl. of the supernatant is removed, leaving approximately 50 µl. of the supernatant in the PCR tube. To this is added 400 µl. of fluorescently labeled detection antibody dilute 1:400 in sample dilution buffer. The pellet and detection antibody are mixed by pipetting and incubated for 30 minutes at room temperature. After this incubation, the conjugated beads are pelleted by centrifugation at 15,000 r.p.m., for 5 minutes at room temperature. The stained conjugated beads are then washed twice with sample dilution buffer. After the final wash the conjugated beads are resuspended in approximately 50 µl. of remaining supernatant and applied to a Guava® flow cytometer for analysis (FIG. 8).

Example 7: Detection Assay

Figure 9:
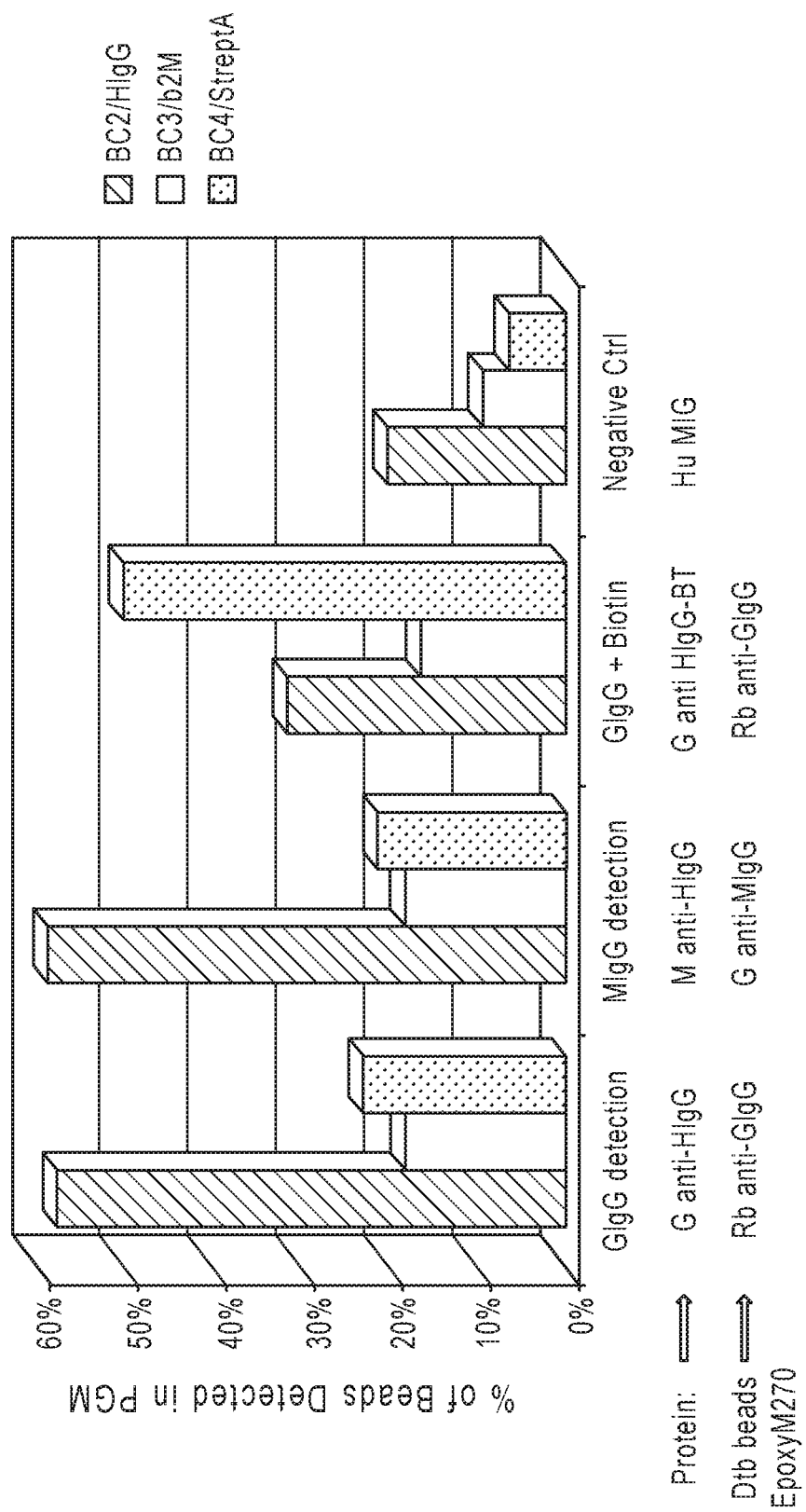
FIG. 9 shows a bar graph depicting the correlation between the percentage of beads sequenced to the expected protein. In all instances, the background level was less than 20%.

The ability to specifically recognize and detect three different analytes in a reaction mixture by FET was tested. Three proteins, human β2-microglobulin, human immunoglobulin, and streptavidin were conjugated (protein approximately $1.8\times10^{-9}$M/$1\times10^9$ beads and $1.5\times10^{-8}$M oligonucleotides/$10\times10^9$ beads) to separate pools of hydrogel beads along with an identifying oligonucleotide barcode using conditions identified above for conjugation. For β2-microglobulin the identifying oligonucleotide was "BC3," for human immunoglobulin "BC2," and for streptavidin "BC4." The selection moieties used included goat anti-human β2-microglobulin, rabbit anti-mouse IgG and goat anti-human IgG. The hydrogel solid supports isolated after contact with a selection moiety were applied to a FET detector for nucleic acid sequence analysis. The correlation between the sequence of the oligonucleotide addressable marker and the protein are depicted in FIGS. 8 and 9. There is a strong correlation between the protein and the expected oligonucleotide addressable marker. At least 500,000 sequence reads were detected.

We claim:

1. A method for detecting one or more analytes in one or more samples, comprising:
   a) providing sample-contacted solid supports comprising a mixture of different populations of solid supports that have been contacted with one or more samples containing one or more analytes, wherein each of the solid supports of each of the different populations of solid supports is attached to a polypeptide ligand that binds an analyte and each of the different populations of solid supports is attached to an addressable oligonucleotide having a barcode sequence, wherein the barcode sequence identifies the polypeptide ligand that is attached to the solid support, and wherein the polypeptide ligands attached to a population of solid supports are the same and the different populations of solid supports have different polypeptide ligands attached thereto;
   b) contacting the sample-contacted solid supports with one or more selection moieties to generate selection moiety-contacted solid supports, wherein each selection moiety binds to one or more of the analytes to which the different polypeptide ligands bind, and each selection moiety is attached to a paramagnetic bead;
   c) separating the selection moiety-analyte-ligand-solid support conjugates from an identifiable solid support-ligand-analyte conjugate that does not bind the selection moiety, using a magnetic source that binds the paramagnetic bead;
   d) releasing the one or more selection moieties from the one or more analytes on the solid support-ligand-analyte-selection moiety conjugates, wherein the addressable oligonucleotide remains attached to the solid support, to generate released addressable solid support conjugate(s);
   e) delivering the released addressable solid supports into an array of microwells, each microwell in the array being capacitively coupled to a sensor that detects a charged species; and
   f) detecting one or more analytes in the one or more samples by detecting a change in charge in one or more microwells of the array.

2. The method of claim 1, wherein the one or more analytes and/or the one or more selection moieties is an antibody.

3. The method of claim 1, wherein detecting the one or more analytes comprises sequencing the barcode sequence of the addressable oligonucleotide of the isolated solid supports in the microwells of the array.

4. The method of claim 1, wherein the one or more analytes is detected by detecting charged species that are the products of an enzymatic reaction.

5. The method of claim 1, wherein the selection moiety-released solid supports are loaded into separate microwells in the array.

6. The method of claim 1, wherein each microwell in the array is capacitively coupled to a sensor which comprises a field effect transistor (FET).

7. The method of claim 1, wherein the barcode sequence of an addressable oligonucleotide of a solid support bound to an analyte that is bound to a selection moiety is sequenced, thereby identifying the analyte.

8. The method of claim 1, wherein the one or more analytes each comprise an antibody that binds an human major histocompatibility complex (hMHC).

9. The method of claim 3, wherein the barcode sequences of the addressable oligonucleotides of the isolated solid supports in the microwells of the array are sequenced simultaneously.

10. The method of claim 7, wherein the barcode sequences of addressable oligonucleotides of solid supports bound to an analyte that bound to a selection moiety are sequenced simultaneously.

11. The method of claim 1, wherein the polypeptide ligands attached to the different populations of solid supports are selected from among HLA1, HLA2, HLA3 and HLA4.

* * * * *

SEQUENCE LISTING

<160> NUMBER OF SEQ ID NOS: 4

<210> SEQ ID NO 1
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 1
cacgctcatc gttaccttag ctgagtcgga gacacgcagg gatgagatgg          50

<210> SEQ ID NO 2
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 2
cacgctcatc gttctcctta ctgagtcgga gacacgcagg gatgagatgg          50

<210> SEQ ID NO 3
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 3
cacgctcatc gaatcctctt ctgagtcgga gacacgcagg gatgagatgg          50

<210> SEQ ID NO 4
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 4
cacgctcatc gatcttggta ctgagtcgga gacacgcagg gatgagatgg          50